(12) United States Patent
Pelissier et al.

(10) Patent No.: US 10,779,801 B2
(45) Date of Patent: Sep. 22, 2020

(54) ULTRASOUND APPARATUS WITH IMPROVED HEAT DISSIPATION AND METHODS FOR PROVIDING SAME

(71) Applicant: Clarius Mobile Health Corp., Burnaby (CA)

(72) Inventors: Laurent Pelissier, North Vancouver (CA); Kwun-Keat Chan, Vancouver (CA); Binda Zhang, Burnaby (CA); Daniel Rahardja, Burnaby (CA)

(73) Assignee: Clarius Mobile Health Corp., Burnaby, British Columbia (CA)

( * ) Notice: Subject to any disclaimer, the term of this patent is extended or adjusted under 35 U.S.C. 154(b) by 172 days.

(21) Appl. No.: 15/271,678

(22) Filed: Sep. 21, 2016

(65) Prior Publication Data

US 2018/0078240 A1    Mar. 22, 2018

(51) Int. Cl.
*A61B 8/00* (2006.01)
(52) U.S. Cl.
CPC ............ *A61B 8/546* (2013.01); *A61B 8/4209* (2013.01); *A61B 8/4444* (2013.01); *A61B 8/4472* (2013.01); *A61B 8/4494* (2013.01); *A61B 2562/12* (2013.01)
(58) Field of Classification Search
CPC ....................................................... A61B 8/546
See application file for complete search history.

(56) References Cited

U.S. PATENT DOCUMENTS

| | | | |
|---|---|---|---|
| 5,213,103 A | 5/1993 | Martin et al. | |
| 5,560,362 A | 10/1996 | Sliwa, Jr. et al. | |
| 5,721,463 A | 2/1998 | Snyder | |
| 5,767,810 A | 6/1998 | Hagiwara et al. | |
| 5,884,693 A | 3/1999 | Austin et al. | |

(Continued)

FOREIGN PATENT DOCUMENTS

CN          205684415 U   * 11/2016
JP          2006130163 A  *  5/2006

(Continued)

OTHER PUBLICATIONS

Chiang, Alice, PC-Based Ultrasound Imaging System in a Probe, 2000 IEEE Ultrasonics Symposium. Proceedings. An International Symposium (Cat. No. 00CH37121) Date of Conference: Oct. 22-25, 2000, Date Added to IEEE Xplore: Aug. 6, 2002.*

(Continued)

*Primary Examiner* — Amelie R Davis
*Assistant Examiner* — John Denny Li
(74) *Attorney, Agent, or Firm* — Julian Ho

(57) ABSTRACT

The present embodiments relate generally to ultrasound apparatus with improved heat dissipation and methods for providing same. The ultrasound apparatus may have a housing that encloses a transducer array and at least one integrated circuit (IC) for driving the transducer array during operation. The housing may have an interior surface and an exterior surface, and the housing can be made substantially of metal. A post is disposed between the at least one IC and the interior surface of the housing. The post can be coupled directly to the interior surface of the housing so that heat generated from the at least one IC is transferred via the post to the housing and dissipated via the exterior surface.

22 Claims, 14 Drawing Sheets

(56) References Cited

U.S. PATENT DOCUMENTS

| | | | |
|---|---|---|---|
| 5,961,465 A | 10/1999 | Kelly, Jr. et al. | |
| 6,198,642 B1* | 3/2001 | Kociecki | H02M 1/4225 |
| | | | 307/150 |
| 6,542,846 B1 | 4/2003 | Miller et al. | |
| 6,610,011 B2 | 8/2003 | Emery | |
| 6,905,466 B2 | 6/2005 | Salgo et al. | |
| 7,298,067 B1 | 11/2007 | Kosinski | |
| 7,400,079 B2 | 7/2008 | Omura et al. | |
| 8,054,231 B2 | 11/2011 | Ahn et al. | |
| 8,475,375 B2 | 7/2013 | Smith et al. | |
| 8,695,429 B2 | 4/2014 | Urbano et al. | |
| 8,748,321 B2 | 6/2014 | deVilliers et al. | |
| 8,784,321 B2 | 7/2014 | Courtney et al. | |
| 9,197,011 B2 | 11/2015 | McCormack | |
| 2004/0215079 A1 | 10/2004 | Omura et al. | |
| 2005/0075573 A1 | 4/2005 | Park et al. | |
| 2005/0122271 A1* | 6/2005 | Pecora, Jr. | H01Q 1/40 |
| | | | 343/719 |
| 2005/0129928 A1* | 6/2005 | Lee | B82Y 30/00 |
| | | | 428/323 |
| 2005/0215892 A1 | 9/2005 | Emery et al. | |
| 2006/0139880 A1* | 6/2006 | Tate | G06F 1/20 |
| | | | 361/697 |
| 2006/0173344 A1 | 8/2006 | Marian et al. | |
| 2007/0071266 A1* | 3/2007 | Little | A61B 8/00 |
| | | | 381/328 |
| 2008/0114252 A1 | 5/2008 | Randall et al. | |
| 2008/0188755 A1* | 8/2008 | Hart | A61B 8/00 |
| | | | 600/459 |
| 2008/0194964 A1* | 8/2008 | Randall | A61B 8/00 |
| | | | 600/459 |
| 2008/0214938 A1 | 9/2008 | Solomon et al. | |
| 2009/0043203 A1 | 2/2009 | Pelissier et al. | |
| 2009/0153409 A1 | 6/2009 | Chiang et al. | |
| 2010/0160785 A1* | 6/2010 | Poland | A61B 8/00 |
| | | | 600/459 |
| 2010/0201226 A1 | 8/2010 | Boström | |
| 2010/0228162 A1 | 9/2010 | Sliwa et al. | |
| 2010/0321253 A1 | 12/2010 | Ayala Vazquez et al. | |
| 2011/0018395 A1 | 1/2011 | Ruffa | |
| 2011/0050508 A1 | 3/2011 | Guterman et al. | |
| 2011/0230794 A1 | 9/2011 | van Groningen et al. | |
| 2012/0071710 A1 | 3/2012 | Gazdzinski | |
| 2012/0150038 A1* | 6/2012 | Osawa | G01S 7/5208 |
| | | | 600/443 |
| 2012/0240769 A1 | 9/2012 | Gerner et al. | |
| 2013/0286593 A1 | 10/2013 | Cho et al. | |
| 2014/0058270 A1* | 2/2014 | Davidsen | A61B 8/546 |
| | | | 600/472 |
| 2014/0092559 A1* | 4/2014 | Yamaguchi | H05K 7/20336 |
| | | | 361/700 |
| 2014/0111388 A1 | 4/2014 | Di Nallo et al. | |
| 2015/0102965 A1 | 4/2015 | Irci et al. | |
| 2015/0182200 A1 | 7/2015 | Birglehner et al. | |
| 2015/0253290 A1 | 9/2015 | Fujii et al. | |
| 2015/0303551 A1 | 10/2015 | Su et al. | |
| 2015/0351727 A1 | 12/2015 | Nieminen et al. | |
| 2016/0077059 A1 | 3/2016 | Chung et al. | |
| 2018/0031196 A1* | 2/2018 | Cripps | F21S 41/62 |

FOREIGN PATENT DOCUMENTS

| | | |
|---|---|---|
| WO | 2012156886 A1 | 11/2012 |
| WO | 2014080312 A1 | 5/2014 |
| WO | 2015102673 A1 | 7/2015 |

OTHER PUBLICATIONS

AMD Global Telemedicine, Trans-Vaginal Ultrasound Probe, Mar. 28, 2016, https://web.archive.org/web/20160328221527/https:/www.amdtelemedicine.com/telemedicine-equipment/PDF/AMD_XXX_TransvaginalProbe_lowres.pdf.*

MatWeb Material Property Data, Overview of materials for 7000 Series Aluminum Alloy, http://www.matweb.com/search/DataSheet.aspx?MatGUID=ab9706916818406b80c22b7f39db0c78&ckck=1.*

Machine Translation of JP2006130163 (Year: 2006).*

Monteiro, The Influence of Alloy Element on Magnesium for Electronic Devices Applications—A Review, Jun. 11, 2014, DOI: 10.5772/58460, https://www.intechopen.com/books/light-metal-alloys-applications/the-influence-of-alloy-element-on-magnesium-for-electronic-devices-applications-a-re (Year: 2014).*

Naumann, H. (2010). "Cellular antenna working inside all-metal case", available at http://www.gsm-modem.de/M2M/m2m-faq/cellular-antenna-working-inside-all-metal-case/, last accessed Mar. 2, 2017.

Abstract of Hsiao, F (2014). "Dual-band slot antenna suitable for ultrabook application with metal housing", published in 2014 International Symposium on Antennas and Propagation (ISAP): 317-318. Date of Conference: Dec. 2-5, 2014.

International Search Report and Written Opinion of the International Searching Authority for Corresponding PCT International Application No. PCT/CA2017/051068 filed Sep. 11, 2017.

* cited by examiner

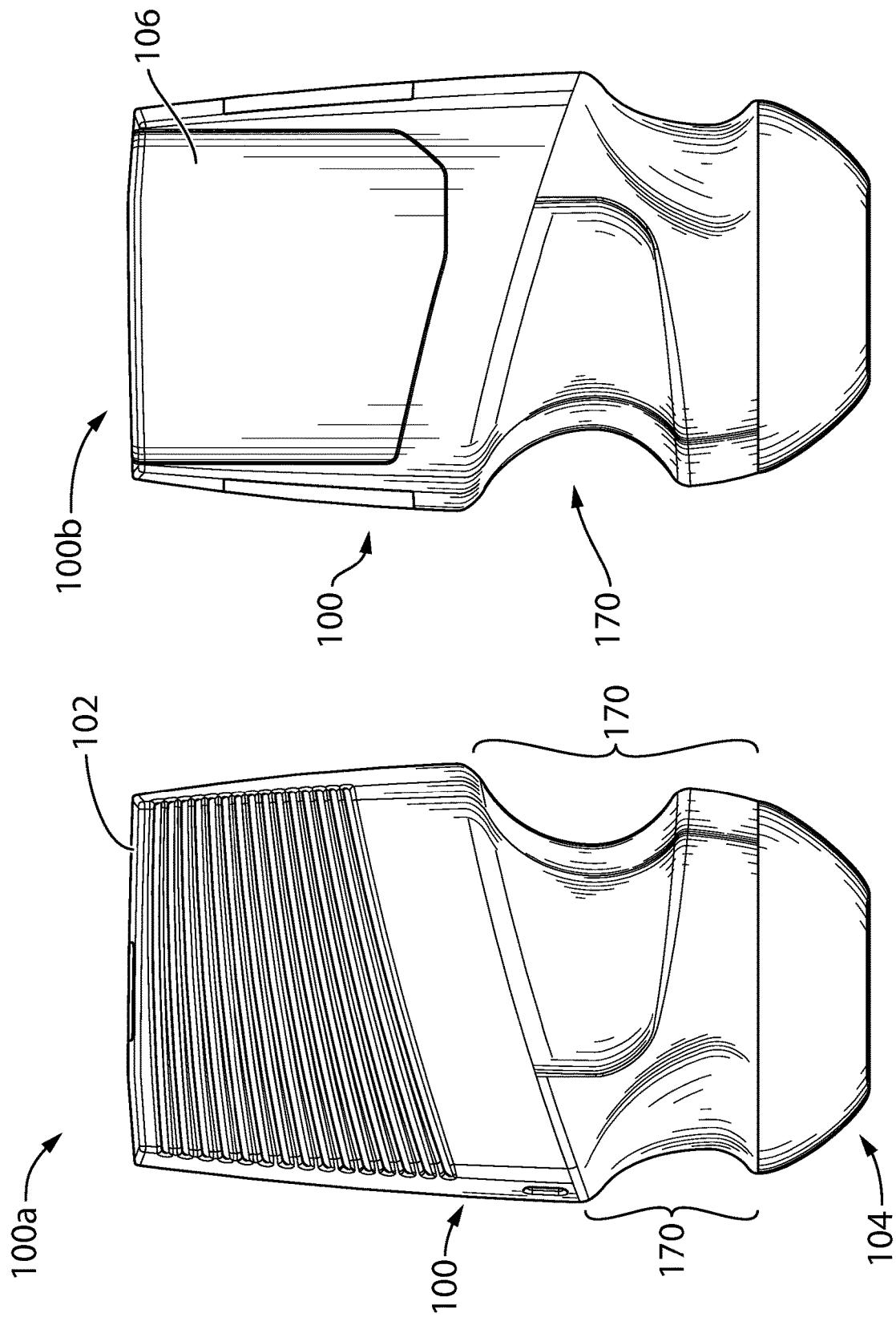

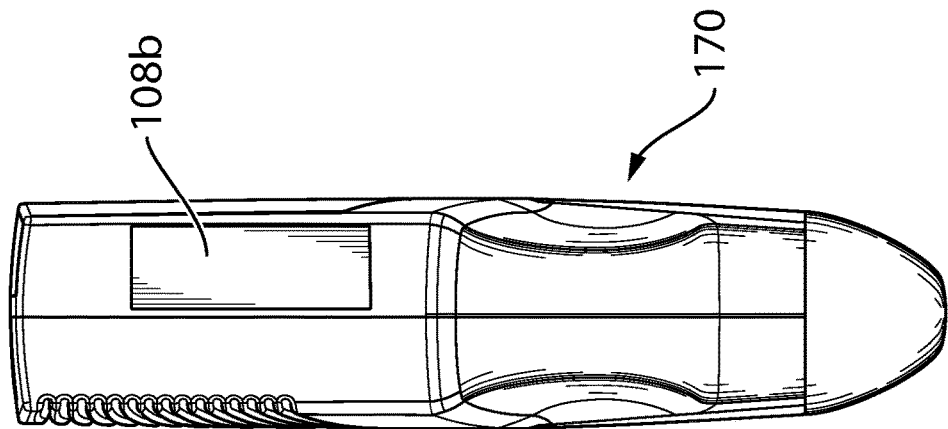
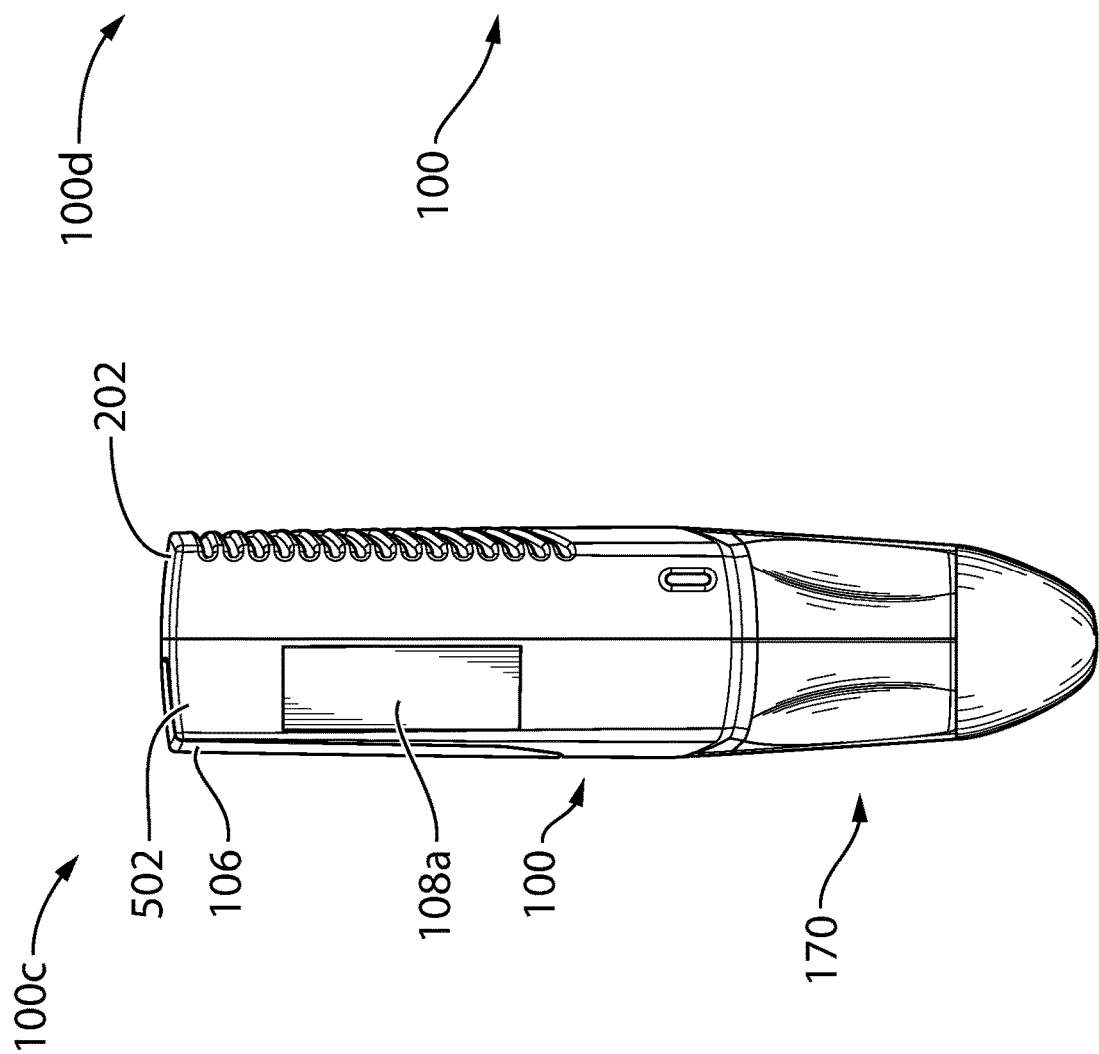
FIG. 1D
FIG. 1C

ULTRASOUND APPARATUS WITH IMPROVED HEAT DISSIPATION AND METHODS FOR PROVIDING SAME

FIELD

The present disclosure relates generally to ultrasound imaging apparatus, and in particular, ultrasound imaging apparatus with improved heat dissipation properties and related methods.

BACKGROUND

Ultrasound imaging systems may generate heat during operation. For example, heat may be generated from the transducer elements in a transducer array when they are activated to transmit ultrasound signals. Also, heat may be generated by integrated circuits (ICs) that drive the transducer array and process imaging data. For example, these ICs may include Analog to Digital Converters (ADCs) that convert the received ultrasound signals into ultrasound images, and/or other ICs (such as graphics processors).

When imaging tissue, ultrasound probes (also called ultrasound transducers) are typically placed against the skin of a patient. To prevent patient injury or discomfort due the probe head having overly high temperatures, there exist regulations that require surfaces of an ultrasound probe to not exceed certain predetermined temperatures while scanning a patient (e.g. International Electrotechnical Commission (IEC) standard 60601 requires external surfaces of an ultrasound probe to not exceed 48° C. in certain conditions).

In a traditional wired ultrasound system, an ultrasound probe may be connected by a cable or wire to a separate ultrasound processing body. Some traditional heat dissipation techniques attempt to channel heat into and through the cable so that it may be dissipated from the cable and/or through the processing body. Such techniques may be particularly effective in wired ultrasound systems because a number of the heat generating components (e.g., the ICs) can be placed within the ultrasound processing body, so as to reduce the amount of heat that needs to be dissipated from the ultrasound probe.

In a wireless ultrasound system, more of the ICs may need to be included within a single wireless ultrasound imaging apparatus or device. Without a cable through which heat can be transferred, wireless ultrasound systems generally have higher heat dissipation requirements. Moreover, to be able to provide high quality ultrasound images, the processing components may operate with heavy loads and/or high frequencies; this further increases the heat generated by a wireless ultrasound imaging device. Despite the higher heat dissipation requirements, wireless ultrasound devices still have to comply with the regulations that require surfaces of an ultrasound probe to not exceed a given temperature.

There is thus a need for ultrasound imaging apparatus with improved heat dissipation properties and related methods.

BRIEF DESCRIPTION OF THE DRAWINGS

Non-limiting examples of various embodiments of the present disclosure will next be described in relation to the drawings, in which:

FIGS. 1A-1D show front, rear, and side views of an ultrasound imaging device, in accordance with at least one embodiment of the present invention;

DETAILED DESCRIPTION

Figure 2A:
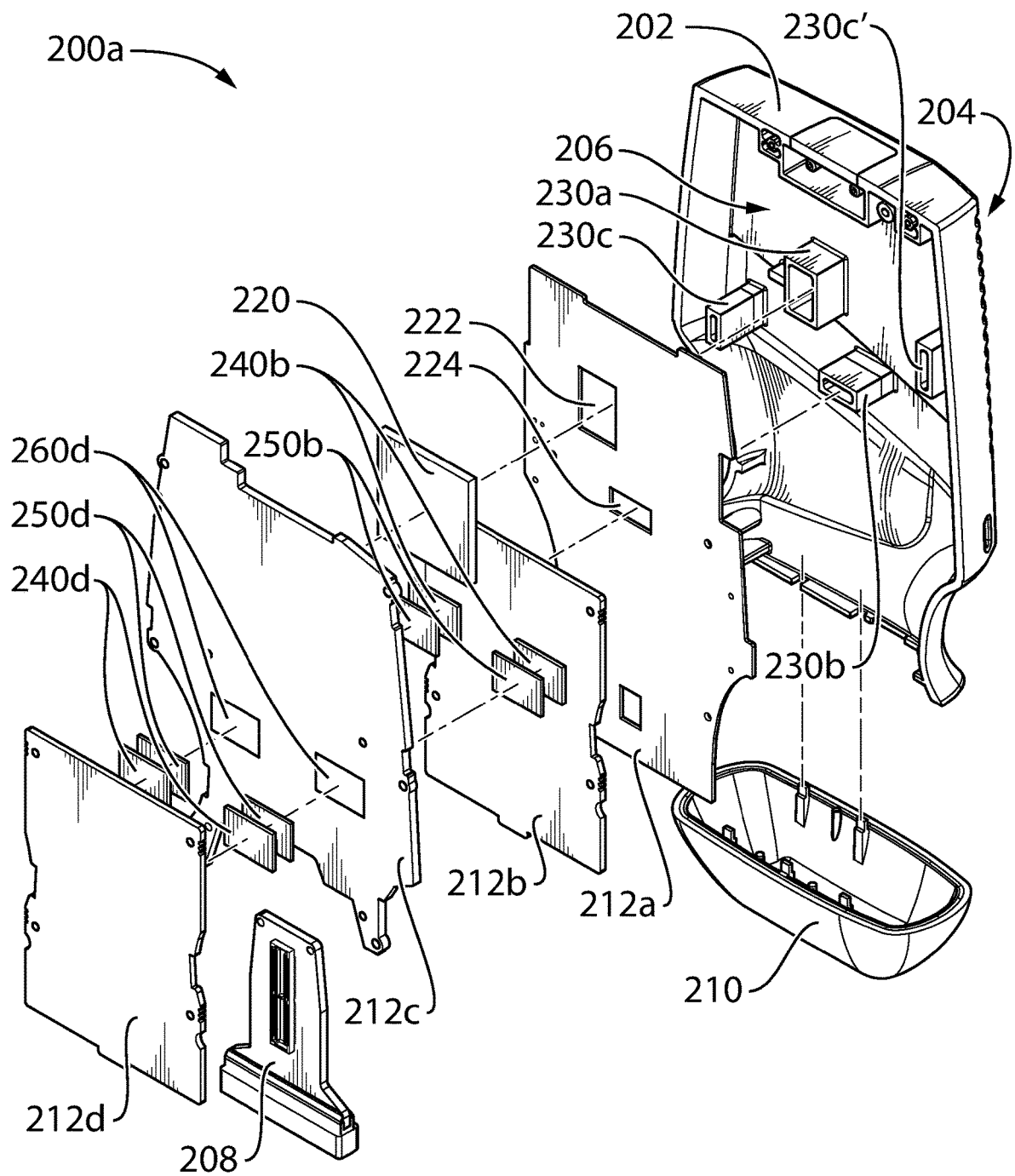
FIG. 2A shows a rear perspective exploded view of some of the components in the ultrasound imaging device of FIGS. 1A-1D, in accordance with at least one embodiment of the present invention.

In a first broad aspect of the present disclosure, there is provided an ultrasound imaging apparatus, including: a housing enclosing a transducer array and at least one integrated circuit (IC) for driving the transducer array during operation of the ultrasound imaging apparatus, wherein the housing includes an interior surface and an exterior surface, and the housing is made substantially of metal; wherein a post is disposed between the at least one IC and the interior surface of the housing, the post being coupled directly to the interior surface of the housing so that heat generated from the at least one IC is transferred via the post to the housing and dissipated via the exterior surface.

In some embodiments, the post is made of the metal. In some embodiments, the post is coupled directly to the at least one IC. In some embodiments, the post is in indirect physical contact with the at least one IC through at least one or more intermediate circuit boards.

In some embodiments, the ultrasound imaging apparatus further includes a circuit board having: a surface facing the interior surface of the housing, and a surface not facing the interior surface of the housing, and the at least one IC is coupled directly to the surface of the circuit board not facing the interior surface of the housing; wherein the post is coupled directly to an area on the surface of the circuit board facing the interior surface of the housing, the area being proximately opposite the at least one IC.

In some embodiments, the thermal conductivity of the housing is at least 55 watts per meter kelvin (W/(m·K)). In some embodiments, the density of the metal or material forming the housing is less than 5 grams per cubic centimeter (g/cm$^3$).

In some embodiments, the post and the housing form part of a unitary body, and the unitary body is created by at least one of: injection moulding, die casting, and machining. In some embodiments, the post is formed separately from the housing, and the post is attached to the interior surface of the housing.

In some embodiments, the housing includes a grip portion and the grip portion is covered with a polymer-based material.

In some embodiments, the exterior surface of the housing includes a plurality of fins. In some embodiments, the fins are made of the metal. In some embodiments, the plurality of fins increases a surface area of the exterior surface of the housing by at least 30%.

In some embodiments, the plurality of fins are positioned on a region of the exterior surface opposite a location on the interior surface that is directly coupled to the post.

In some embodiments, the region of the exterior surface having the plurality of fins have a first size and the location on the interior surface that is directly coupled to the post has a second size, and the first size is larger than the second size.

In some embodiments, the ultrasound imaging device further includes a first side of the ultrasound imaging apparatus and a second side of the ultrasound imaging apparatus opposite the first side, and wherein the fins are positioned on the first side of the ultrasound apparatus and a battery for powering the ultrasound imaging apparatus is positioned on the second side of the ultrasound imaging apparatus.

In some embodiments, the exterior surface of the housing has a surface area of at least 10,000 square millimeters (mm$^2$).

In some embodiments, the at least one IC consumes at least 3 watts of power while imaging.

In some embodiments, the housing protects from ingress into an interior of the ultrasound imaging apparatus, and the housing has an International Protection Marking of at least IPX7.

In some embodiments, the housing includes an opening that allows for the at least one IC to connect to an antenna positioned on the exterior surface of the housing.

In another broad aspect of the present disclosure, there is provided a method of facilitating dissipation of heat in an ultrasound imaging apparatus, the method including: providing a housing for the ultrasound imaging apparatus, the housing enclosing a transducer array and at least one integrated circuit (IC) for driving the transducer array during operation of the ultrasound imaging apparatus, wherein the housing includes an interior surface and an exterior surface, and the housing is made substantially of metal; and activating the at least one IC during operation of the ultrasound imaging apparatus, wherein heat generated from the at least one IC is transferred to the housing and dissipated by the exterior surface via at least one post that is disposed between the at least one IC and the interior surface of the housing, the post being coupled directly to the interior surface of the housing.

In some embodiments, the exterior surface of the housing includes a plurality of fins.

In another broad aspect of the present disclosure, there is provided a housing for an ultrasound imaging apparatus, the housing for enclosing a transducer array and at least one integrated circuit (IC) for driving the transducer array during operation of the ultrasound imaging apparatus, the housing including: an interior surface configured to receive a post, the post being positionable between the at least one IC and the interior surface of the housing; and an exterior surface, wherein heat generated from the at least one IC is transferable via the post to the housing and the heat is dissipated via the exterior surface.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIGS. 1A-1D shown there generally as 100*a*, 100*b*, 100*c*, 100*d* respectively are front, rear, left side, and right side views of an ultrasound imaging device, in accordance with at least one embodiment of the present invention. FIG. 1A shows the front view of the ultrasound imaging device 100. The ultrasound imaging device 100 generally has a housing 102 which contains a transducer array and the processing components. The transducer array may be positioned near a bottom portion 104 of the housing 102. As the ultrasound imaging device 100 is used to perform imaging, heat may be generated by the transducer array and/or the processing components within the housing 102. In various embodiments, a grip portion 170 may be provided (e.g., to facilitate easier holding of the ultrasound imaging device 100). In the specific example embodiment illustrated, the grip portion 170 may be shaped in a manner that (alone or in combination with other visual elements) primarily provides a distinctive visual and decorative appearance for the ultrasound imaging device 100.

FIG. 1B shows the rear view of the ultrasound imaging device 100. In the illustrated embodiment, an upper portion of the rear portion of the housing 102 may hold a removable battery 106 for powering the ultrasound imaging device 100. In various embodiments, the shape, positioning, and appearance of the battery 106 when it is secured to the ultrasound imaging device 100 may take different forms. However, in the example embodiment illustrated, the shape of the battery 106 and its appearance when it interfaces with the ultrasound imaging device 100 primarily provides (alone or in combination with other visual elements) a distinctive visual and decorative appearance for the ultrasound imaging device 100. As illustrated, the grip portion 170 may be shaped to extend to the rear of the ultrasound imaging device 100.

FIG. 1C shows a left side view of an example embodiment of an ultrasound imaging device 100. The housing 102 may be made up of a front shell 202 that mates with a rear shell 502. Shown also in FIG. 1C is the removable battery 106 in the attached position. To allow for improved heat dissipation, the housing 102 may be made substantially of metal.

For example, the metal may be made of aluminum or magnesium, and/or a related alloy or composite. In some embodiments, the housing 102 is made of a magnesium composite having at least 50% magnesium. In some embodiments, the magnesium alloy AZ91D is used to form some or all of the housing 102. Additionally or alternatively, in some embodiments, the magnesium alloy AZ31B may be used to form some or all of the housing 102. Further, in some embodiments, aluminum 6061 may be used to form some or all of the housing 102.

The thermal conductivity characteristics of materials can be used as a way to identify a suitable material to form the housing 102. For example, aluminum 6061 may have a relatively high thermal conductivity of 167 watts per meter kelvin (W/(m·K)), whereas the noted magnesium alloys may generally have lower thermal conductivity (e.g., AZ91D has thermal conductivity of 72.3 W/(m·K), and AZ31B has thermal conductivity of 96 W/(m·K)). Thus, in some embodiments, aluminum 6061 may be selected for the material to be used to form the housing 102 (e.g., if optimal thermal performance is desired).

However, in additional embodiments, it may be possible to select the material for the housing 102 not solely upon thermal performance but also upon additional characteristics of the material such as density (which may affect the overall weight of the ultrasound imaging device 100) and/or the suitability of the material for mass production processes such as die casting. For example, whereas aluminum 6061 may provide optimal thermal conductivity performance, aluminum 6061 also has a higher density at 2.71 grams per cubic centimeter ($g/cm^3$). In contrast, the noted magnesium alloys generally have lower thermal conductivity performance, but also a lower density (e.g., AZ91D has a density of 1.9 $g/cm^3$, and AZ31B has a density of 1.77 $g/cm^3$). In embodiments where it is desirable to find a balance between a material that provides sufficient thermal conductivity and also does not unduly increase the overall weight of ultrasound imaging device 100, the noted example magnesium alloys may be used. For example, it may be desirable to select AZ91D over aluminum 6061 because the reduction of the density from 2.71 $g/cm^3$ to 1.9 $g/cm^3$ provides roughly a 30% decrease in the weight of the housing 102, while still providing acceptable thermal conductivity performance. Overall, the thermal conductivity of the material selected to form the housing 102 may be at least 55 W/(m·K) and/or the density of the material selected to form the housing may be less than 5 $g/cm^3$.

With respect to suitability for mass production processes, it will be understood by persons skilled in the art that there may be multiple ways of producing the parts (e.g., the front shell 202 and/or rear shell 502) that form the housing 102. For example, it may be possible to machine the parts (e.g., use a piece of raw material and cut it into a desired final shape and size using a controlled material-removal process such as a Computer Numeric Control (CNC) automated machine). Alternatively, it may be possible to create the part using die casting (e.g., to form the part by pouring molten metal into a mold), which is typically used for mass production. As between the different example magnesium alloys discussed herein, AZ91D may be more suitable for die casting over AZ31B (which is more suitable for machining); although any one or more of machining, injection moulding, die casting, or any other suitable production method may be used for providing the parts for the housing 102.

Traditional ultrasound probes are typically constructed with a housing made substantially of heat insulating material (e.g., a polymeric material such as plastic). This is to prevent surfaces of the ultrasound probe from experiencing high temperatures, so as to be non-compliant with regulations that require external surfaces of an ultrasound probe to be lower than a predetermined temperature. In such probes, heat is primarily channeled towards the non-imaging end of the ultrasound probe, where there is a cable through which the heat can be transferred and dissipated (e.g., in a wired ultrasound system) or where there is a localized heatsink for absorbing and/or dissipating the heat.

Figure 2B:
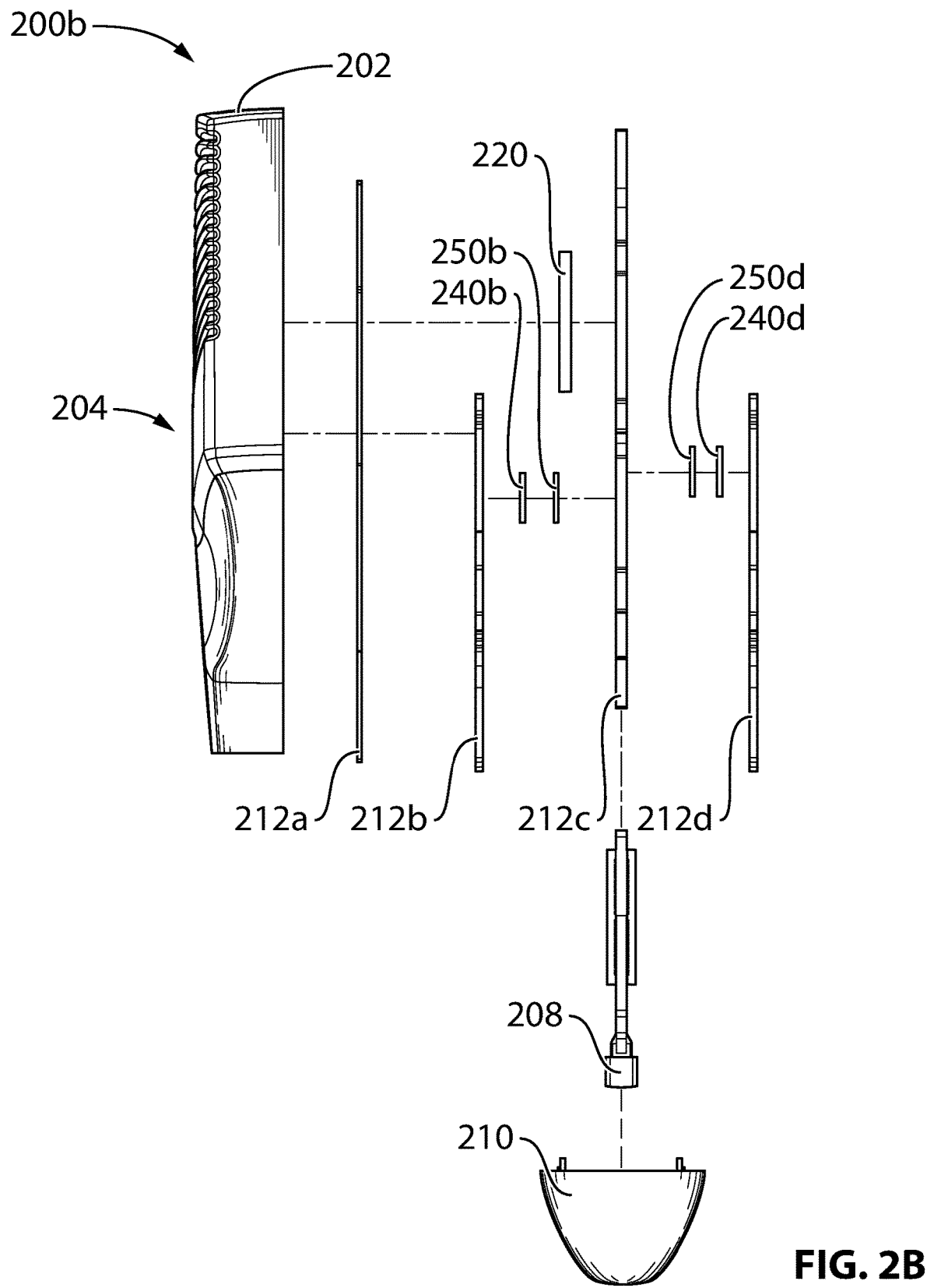
FIG. 2B shows a side exploded view of the ultrasound imaging device of FIGS. 1A-1D, in accordance with at least one embodiment of the present invention.
Figure 2C:
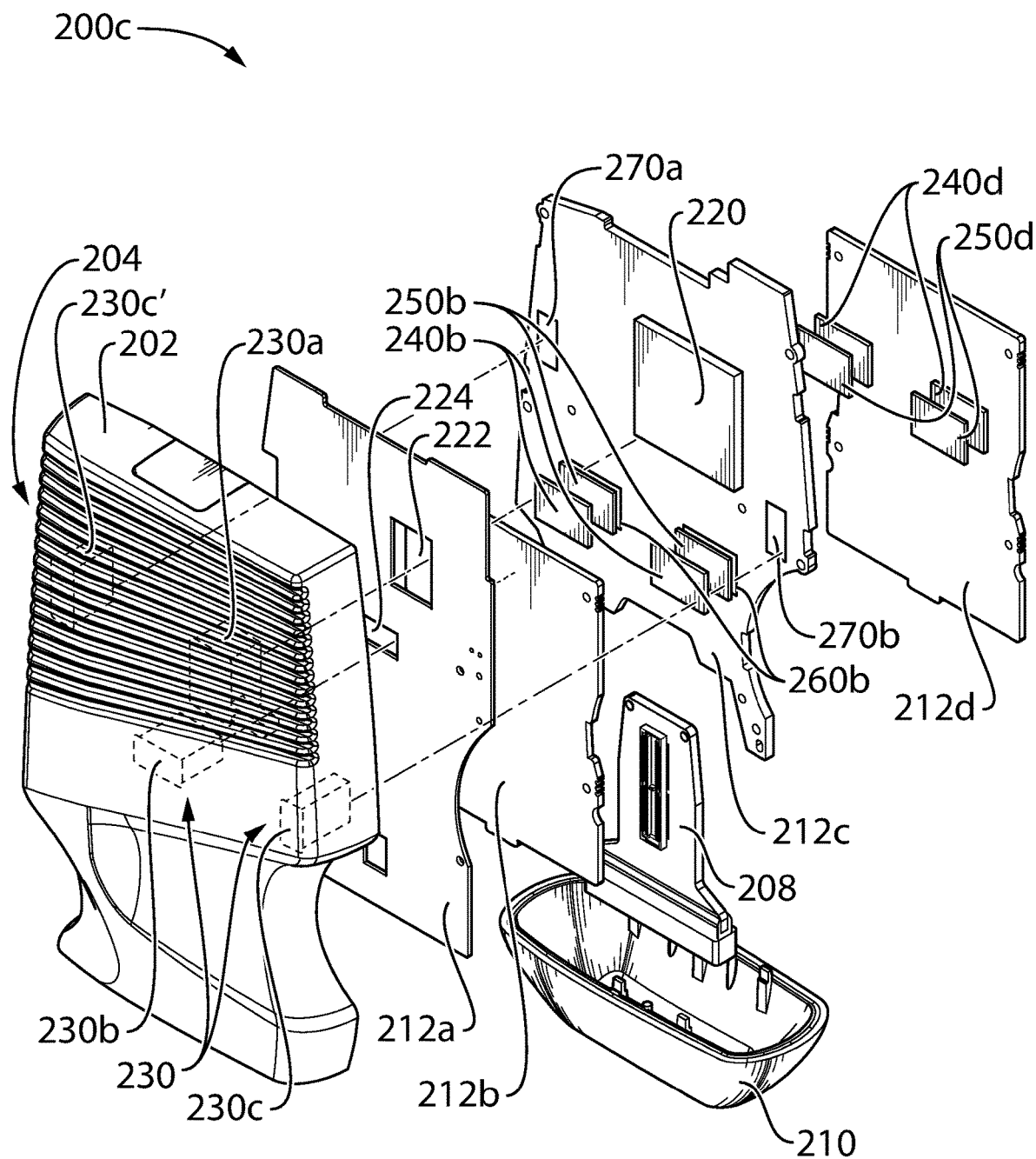
FIG. 2C shows a front perspective exploded view of the ultrasound imaging device of FIGS. 1A-1D, in accordance with at least one embodiment of the present invention.

In the present embodiments, a substantial portion of the housing 102 is made of metal (except for the transducer array cap 210 (as shown in FIGS. 2A-2C)). This allows almost the entire surface area of the ultrasound imaging device 100 to act as a heatsink and dissipate heat. This larger surface area may dissipate more heat than any localized heatsink, so as to lower the overall heat retained in the ultrasound imaging device 100. In turn, this reduces the likelihood that any single exterior surface of the ultrasound imaging device 100 (or region thereof) would experience overly high temperatures that would cause non-compliance with applicable regulations.

For example, in the embodiments discussed herein, a significant portion of the heat may be generated by ICs (e.g., the ADCs and graphic processors) provided within the housing 102; and as discussed below, posts may be added to extend from an interior surface of the housing 102 to assist with drawing heat away from the ICs towards the exterior surface of the housing 102 for improved heat dissipation. Due to the heat generated by the ICs, traditional ultrasound transducer designs may generally avoid the use of metal on the exterior surface of the housing 102 because metal may be warmer to the touch (and thus be more vulnerable to non-compliance with applicable regulations) than other materials such as plastic. However, by having a substantial portion of the housing 102 be made of metal, the heat generated by the ICs may be able to be spread more evenly throughout the housing 102. As a result, the present embodiments may be less likely to experience any localized hotspots that make the device non-compliant with applicable regulations.

In some embodiments, substantially all of the exterior surface of the metallic housing 102 may be exposed to air. In alternative embodiments, certain parts of the housing 102 may be selectively covered with a layer of rubber or similar material. For example, in some embodiments, the grip portion 170 may be covered with a thin layer of rubber. The rubber material may make the ultrasound imaging device 100 less slippery and easier to grip. Additionally, by targeting a limited area of the overall metallic housing 102 to be covered with the rubber material, such embodiments limit the insulating impact of the rubber cover to the targeted area (e.g., the grip portion 170) while still allowing a significant portion of the remaining metallic housing 102 to be exposed to air for enhanced heat dissipation. Further, the rubber cover on the grip portion 170 may reduce the heat sensation felt by ultrasound operators and allow operators to hold the device for longer periods of time. In doing so, the hand holding the ultrasound imaging device 100 may serve as a heat sink (e.g., a heat sink additional to the heat radiating into the ambient air from the remaining exposed metal portions of the housing 102) for longer periods.

In various embodiments, the percentage of the total exterior surface area of the metal housing 102 covered by the rubber layer may be 0%-49%. For example, in the illustrated example embodiments, the overall surface area of the metallic housing 102 may be approximately 31,525 millimeters squared (mm²). However, the surface area of the grip portion 170 may be approximately 12,164 mm², so that the remaining non-rubber-covered surface area of the metallic housing 102 is approximately 19,361 mm². In this embodiment, the rubber-covered grip portion 170 thus constitutes approximately 38.6% of the external surface area of the housing 102, while the non-rubber covered portion of the housing 102 constitutes substantially more than half of the remaining exposed surface of the metallic housing 102 (e.g., approximately 61.4% of the surface area of the housing 102). It will be understood by persons skilled in the art that other configuration of targeted rubber covering of selected portions of the housing 102 are possible. For example, an ultrasound imaging device 100 configured with a smaller grip portion 170 may have a smaller percentage of the overall surface area of the housing 102 be covered by rubber. While the use of a rubber covering is discussed herein, in various embodiments, the cover may be made of any suitable polymer-based material. For example, any one or more of polyurethane, thermoplastic elastomer, and/or silicone may be used in addition to, or instead of, rubber as the material for the covering.

Moreover, the embodiments described herein may include other configurations of ultrasound imaging devices with metal housings 102 that have a variety of different surface area measurements, so long as the heat dissipation techniques described herein are practised. For example, in some embodiments, the exterior surface of the metal housing 102 of an ultrasound imaging device 100 may have a surface area of at least 10,000 mm².

Referring still to FIG. 1C, a recess may be provided on an exterior surface of the housing 102 to allow for placement of an antenna that allows for wireless communications. As shown, a recess is provided under a cover 108a, under which suitable antennas for wireless communications may be placed. In some embodiments, to allow for improved wireless communication performance and/or capacity, the housing 102 may be provided with multiple recesses to allow for placement of multiple antennas. FIG. 1D shows a right side view of the ultrasound imaging device 100, which has a recess similar to that which is on the left side of the ultrasound imaging device 100 and is covered by a cover 108b. The grip portion 170 is also shown in FIGS. 1C and 1D. Further details of the placement of the antenna within the recesses are discussed below in relation to FIGS. 6A, 6B, and 7.

Referring to FIG. 2A, shown there generally as 200a is a rear perspective exploded view of some of the components in the ultrasound imaging device of FIGS. 1A-1D, in accordance with at least one embodiment of the present invention. As shown, the front shell 202 (forming part of the housing 102 shown in FIG. 1A) may have an exterior surface 204 and an interior surface 206. A number of posts 230a, 230b, 230c, 230c' may be coupled directly to the interior surface 206 of the front shell 202 to allow heat generated by ICs to be transferred via the posts 230a, 230b, 230c, 230c' to the housing 102 and dissipated via the exterior surface 204. As shown, the exterior surface 204 may be exposed to open air (e.g., without any covering) to facilitate improved heat dissipation.

In the illustrated embodiment, there may be a number of circuit boards 212a, 212b, 212c, 212d which form an assembly and can be mated with the front shell 202. The transducer array 208 may be coupled to the circuit boards 212a, 212b, 212c, 212d, and in completely assembled from, the transducer array 208 may be covered with a transducer cap 210.

As shown with dotted connection lines in FIG. 2A, the circuit board 212a may be provided with openings 222, 224 or cut-outs that fit around the posts 230a, 230b, 230c, 230c'. For example, the opening 222 may be shaped so as to fit around post 230a, and opening 224 may be shaped to fit around post 230b. The post 230a may then have direct physical contact with an IC (e.g., processor 220) provided on circuit board 212c. In some embodiments, thermal paste may be provided on the processor 220 to increase the thermal coupling between the processor 220 and the post 230a. Thermal paste or grease may be usable in various scenarios described herein. An example thermal grease that can be used herein is Hydronaut™ thermal paste available from Thermal Grizzly™. However, it will be understood that any other suitable thermal paste or grease may be used instead.

To convert the analog ultrasound information received by the ultrasound transducer 208 into digital signals, a number of ADCs 240b, 240d may be positioned on circuit boards 212b, 212d respectively. As shown, the ADCs 240b are provided on the surface of the circuit board 212b which faces circuit board 212c.

The ADCs 240b may heat up the upper region of circuit board 212b. To provide improved dissipation of the heat present on the upper region of circuit board 212b, the post 230b may mate with an area on the surface of the circuit board 212b that is opposite the ADCs 240b and facing the interior surface 206 of the front shell 202. As illustrated with dotted connection lines, the post 230b may protrude through opening 224 in circuit board 212a to mate with an area of the upper region of board 212b that is proximately opposite the ADCs 240b. However, in alternative embodiments, the post 230b may be configured to mate to circuit board 212b at an area that is directly opposite the ADCs 240b (e.g., if the position of the ADCs 240b are moved towards the top of the circuit board 212b or if the post 230b and the opening 224 is moved lower to mate with an area on the surface of the circuit board 212b that is directly opposite the ADCs 240b). Similar to the post 230a, the post 230b mating with circuit board 212b helps to draw heat away from the upper region of the circuit board 212b (which, in turn, may experience high temperatures due to the heavy loads being processed by the ADCs 240b) towards the front shell 202 for dissipation through the exterior surface 204. In some embodiments, thermal paste may also be used to improve the thermal coupling between the post 230b and where it mates with the surface of the circuit board 212b facing the front shell 202.

Configuring posts 230 to couple directly to a heat source such as an IC (as is the case for post 230a) may generally be considered the most efficient way to draw heat away from the IC. While introducing an intermediate medium such as a circuit board 212b in between the heat source (e.g., ADCs 240b) and the post 230b may slightly reduce the efficiency of the heat transfer, the degradation in heat transfer efficiency may be minimal in embodiments where the ultrasound imaging device 100 is small and enclosed. For example, this may be because the small and enclosed nature of the ultrasound imaging device 100 will cause the temperature of almost all the components within the housing 102 to reach a similar level in a relatively short period of time. This may enable the circuit board 212b to transfer heat to the post 230*b* with a thermal transfer efficiency that is similar to scenarios where the ICs are coupled directly to a post 230.

To further improve the dissipation of heat generated by ADCs 240*b*, the ADCs 240*b* may mate directly with portions of the circuit board 212*c* (shown with dotted connection lines in FIG. 2A). As discussed in greater detail below with respect to FIG. 2C, heat may transfer through the ground plane of the circuit board 212*c* and be transferred to posts 230*c*, 230*c*', which may be mated with the circuit board 212*c* at another area of the board 212*c* other than where the ADC 240*b* mates with circuit board 212*c*. As with the post 230*b*, the posts 230*c*, 230*c*' helps to transfer the heat generated by the ADCs 240*b* to the housing 202 so that it can be dissipated by the exterior surface 204.

Various techniques may be used to facilitate the mating of ADCs 240*b* to the circuit board 212*c*. As shown in FIG. 2A, thermal pads 250*b* are used to provide coupling and thermal conductivity between the ADCs 240*b* and the circuit board 212*c*. However, other methods of facilitating thermal coupling (e.g., thermal grease or paste) may also be used. Generally, in various embodiments herein, thermal pads or thermal grease may be used interchangeably. For example, thermal pads may be used to bridge wider gaps, and thermal grease may be used to bridge narrower gaps. However, it will be understood by persons skilled in the art that any combination of one or more of thermal pads, thermal grease, or any other suitable method of providing thermal coupling may be used herein when thermal coupling between components is discussed.

In some embodiments, to provide additional capacity to process received ultrasound signals and provide improved image quality, there may be additional ADCs 240*d* on circuit board 212*d*. As illustrated, these ADCs 240*d* may similarly mate with the circuit board 212*c* via thermal pads 250*d* to allow for improved dissipation of the heat generated by ADCs 240*d*. In FIG. 2A, exposed ground plane areas 260*d* on the circuit board 212*c* are shown. As shown with the dotted connection lines, the ADCs 240*d* may mate to these exposed ground plane areas 260*d* via thermal pads 250*d* to facilitate the transfer of heat from the ADCs 240*d* to the ground plane of circuit board 212*c*. Referring briefly simultaneously to FIG. 2C, similar exposed ground plane areas 260*b* may be provided on the front surface of circuit board 212*c* to allow mating with the ADCs 240*b* on the circuit board 212*b* via thermal pads 250*b*.

Referring to FIG. 2B, shown there generally as 200*b* is a side exploded view of the ultrasound imaging device of FIGS. 1A-1D, in accordance with at least one embodiment of the present invention. Dotted connection lines show how post 230*a* (not shown in FIG. 2B) in front shell 202 may mate with processor 220 provided on circuit board 212*c* through circuit board 212*a*. Similarly, another dotted connection line shows how post 230*b* (not shown in FIG. 2B) may mate with a region of the front surface of circuit board 212*b* that is proximately opposite the ADCs 240*b* which may be provided on circuit board 212*b*. Further dotted connection lines show how ADCs 240*b* provided on circuit board 212*b* may be mated to circuit board 212*c* via thermal pads 250*b*, and how ADCs 240*d* provided on circuit board 212*d* may be mated to circuit board 212*c* via thermal pads 250*d*. The transducer array 208 may be connected to circuit board 212*c* and transducer cap 210 are also shown in FIG. 2B. As discussed, the heat generated by the various components ICs may travel through the posts 230 (not shown in FIG. 2B) to be dissipated via exterior surface 204.

Referring to FIG. 2C, shown there generally as 200*c* is a front perspective exploded view of the ultrasound imaging device of FIGS. 1A-1D, in accordance with at least one embodiment of the present invention. FIG. 2C shows a front view of the front shell 202 of the housing 102 having exterior surface 204, and internal posts 230*a*, 230*b*, 230*c*, 230*c*' shown in dotted outline. FIG. 2C also shows the surfaces of circuit boards 212*a*, 212*b*, 212*c*, 212*d* facing the interior surface 206 of the front shell 202, along with transducer array 208 and transducer cap 210. In FIG. 2C, the processor 220 is shown as being fixed to circuit board 212*c*. As was discussed in relation to FIG. 2A above, a dotted connection line shows how post 230*a* may protrude through circuit board 212*a* via opening 222 so as to mate directly with processor 220 and draw heat away therefrom. Similarly, another dotted connection line shows how post 230*b* may protrude through circuit board 212*a* via opening 224 so as to mate with an area on the surface of circuit board 212*b* that is proximately opposite ADCs 240*b*.

FIG. 2C also shows how ADCs 240*b*, 240*d* may mate with circuit board 212*c* via thermal pads 250*b*, 250*d* respectively. As was the case with the surface of circuit board 212*c* facing away from the interior surface 206 of the front shell 202 (as shown in FIG. 2A), there may be exposed ground plane areas 260*b* on the front surface of the circuit board 212*c* for mating with the ADCs 240*b* on circuit board 212*b* via thermal pads 250*b*.

As viewable in FIG. 2C, dotted connection lines show how exposed ground plane areas 270*a*, 270*b* may be provided to mate with posts 230*c*', 230*c* respectively. Heat generated by the ADCs 240*b*, 240*d* may generally be transferred via the thermal pads 250*b*, 250*d* to the exposed ground plane areas 260*b*, 260*d*. As will be understood by persons skilled in the art, the ground plane of circuit board 212*c* may generally be made of a material that is of high thermal conductivity (e.g., copper). As a result, the heat received by the exposed ground plane areas 260*b*, 260*d* may be transferred through the ground plane of the circuit board 212*c* to the exposed ground plane areas 270*a*, 270*b* that couple with the posts 230*c*', 230*c*. The heat may then further be transferred though the posts 230*c*', 230*c* to the housing 102 (e.g., front shell 202) and dissipated through the exterior surface 204.

In the example embodiment illustrated in FIG. 2C, the post 230*a* is coupled directly to at least one IC (e.g., the processor 220). In contrast, the posts 230*b*, 230*c*, 230*c*' may be considered to be in indirect physical contact with a number of ICs through at least one or more intermediate circuit boards. For example, the post 230*b* may be in indirect contact with the ADCs 240*b* through circuit board 212*b*. Likewise, posts 230*c*, 230*c*' may be considered to be in indirect physical contact with ADCs 240*b*, 240*d* through circuit board 212*c* (and in the illustrated embodiments, also through thermal pads 250*b*, 250*d*).

In contrast with dissipating heat into the internal ambient air for transfer to the housing 102, the posts 230 may provide improved conduits of thermal energy transfer and draw more of the heat generated by the processor 220 or ADCs 240*b*, 240*d*. This may allow for more heat to be transferred to the housing 102 (e.g., front shell 202) for dissipation through the exterior surface 204.

Posts 230 may generally be made of any material that provides improved thermal conductivity over ambient air. In some embodiments, one or more of the posts 230 may be made of the same metal that the front shell 202 (and the housing 102) is made of. The posts 230 being made of the same metal may allow for there to be uniform thermal conductivity as between the posts 230 and the housing 102, so as to facilitate better heat transfer to the housing 102. It may also allow the heat to be spread out evenly across all parts of the same material, so as to reduce the likelihood of concentrated hot spots at any single region of a post 230 (where such hot spots may potentially expose internal ICs to excessive heat and cause damage thereto) or on surfaces of the housing 102 (where such hot spots may cause discomfort to ultrasound operators or cause non-compliance with applicable temperature regulations).

The posts 230 may be formed in different shapes and configurations. For example, the posts 230 may be provided in a circular, square, rectangular, or other shape. Additionally or alternatively, the posts 230 may be constructed as having a solid metal interior or having a hollow interior which can then be filled with thermal paste and/or a solid block of metal. Since the metal may provide improved thermal conductivity over ambient air, a solid metal interior may provide improved heat dissipation over a configuration where there is no post 230 at all. However, to further improve heat transfer, in some embodiments, it may be possible to provide a post 230 that is hollow and filled in with thermal paste. Since thermal paste may have higher thermal conductivity over the metal of the posts 230, the thermal paste provided within the post 230 may further improve heat transfer from the surface to which the post 230 is mated (e.g., a circuit board or an IC) towards the housing 102. Additionally or alternatively, in some embodiments, to provide for structural integrity of a given post 230, the hollow interior of a post 230 may be filled with a solid block of metal that is attached via an adhesive and surrounded by thermal paste.

In addition to considerations about thermal conductivity, the manufacturing process used to create the housing 102 may be taken into account when determining the shape and configuration of the posts 230. For example, when a machining process is used to create the housing 102, it may be suitable to perform the machining in a manner that leaves a solid metal post. However, when a die casting process is used, it may be difficult to achieve a solid metal post with the same thickness that can be obtained via the machining process. As such, when using die casting, it may be suitable to create a mold with a post having a hollow interior (with side walls having a thickness suitable for die casting), which can then be filled in the manner noted above (e.g., with thermal paste or a solid metal block).

Different methods may be used to attach the posts 230 the interior surface 206 of the front shell 202. For example, in some embodiments, one or more of the posts 230 and the housing 102 form part of a unitary body. Such a unitary body may be created by including the posts 230 in the mold used to create the front shell 202 (e.g., if the front shell 202 is created by injection moulding and/or die casting). Additionally or alternatively, separately formed posts 230 may be attached to the front shell 202 at desired locations. For example, the front shell 202 may be formed with slots for receiving one or more of separately formed posts 230, and such posts 230 may be attached using the slots after creation of the front shell 202. In some embodiments, such attachment may be achieved using adhesive (e.g., Loctite™ 435). Thermal paste may also be used to enhance the thermal attachment between the separately formed posts 230 and the slots that receive the posts 230. Referring again briefly to FIG. 2A, it can be seen that in the illustrated embodiment, post 230a is provided as being a unitary part of the front shell 202 (shown with a hollow interior). However, post 230b and 230c are illustrated as separately formed posts (also with hollow interiors) that are attached to slots receiving the posts 230b and 230c. This is why in the illustrated embodiments, there is a line separating the body of the posts 230b, 230c from corresponding slots for receiving the posts 230b, 230c; where such line is not present on post 230a.

Figure 3A:
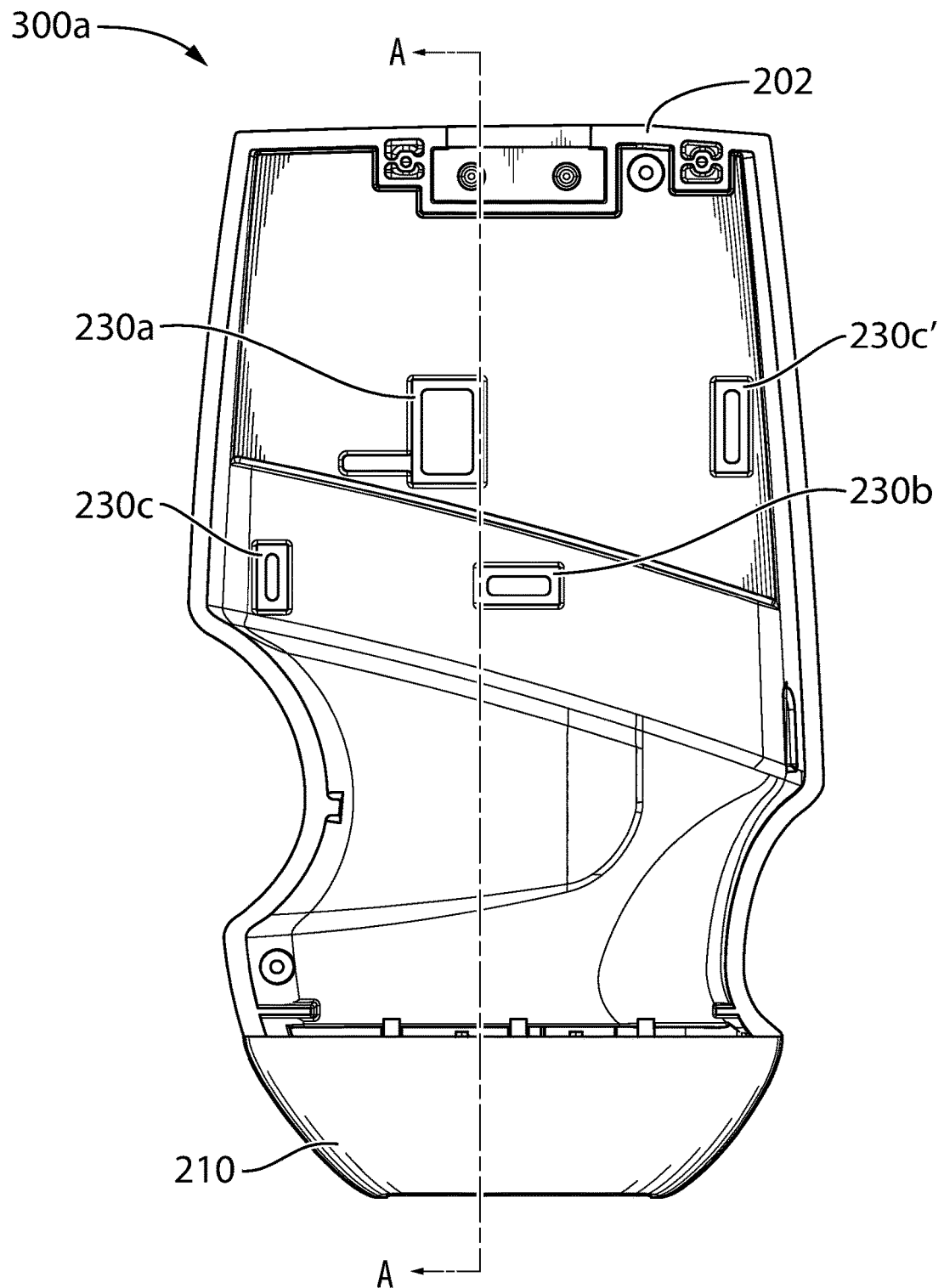
FIG. 3A shows an interior view of the front shell that forms part of the housing of the ultrasound imaging device of FIGS. 1A-1D, in accordance with at least one embodiment of the present invention.

Referring to FIG. 3A, shown there generally as 300a is an interior view of the front shell 202 shown in FIGS. 2A-2C, in accordance with at least one embodiment of the present invention. In FIG. 3A, the front shell 202 is shown only with the transducer cap 210. The interior view of the front shell 202 provides a clear view of the interior surface 206 (as shown in FIG. 2A) of the front shell 202. As a result, posts 230a, 230b, 230c, 230c' can be seen.

Figure 3B:
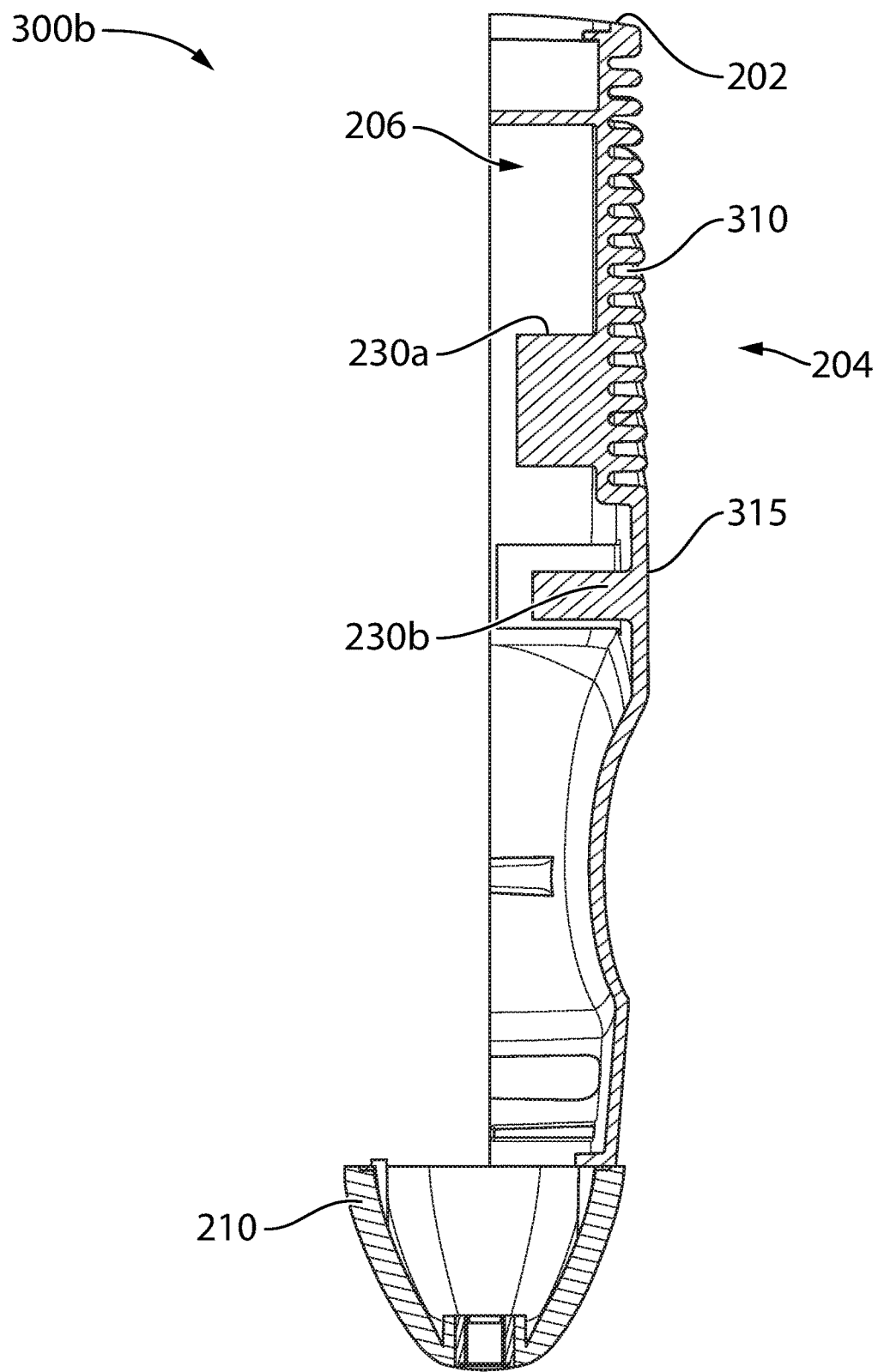
FIG. 3B shows a cross-sectional view of the front shell of FIG. 3A, along line A-A shown in FIG. 3A, in accordance with at least one embodiment of the present invention.

Referring to FIG. 3B, shown there generally as 300b is a cross-sectional view of the front shell of FIG. 3A, along line A-A shown in FIG. 3A, in accordance with at least one embodiment of the present invention. In the illustrated embodiment, it can be seen that the exterior surface 204 of the front shell 202 may be configured to have a number of fins 310. At the same time, certain regions 315 of the exterior surface 204 may be configured to have a smooth surface without any fins 310.

The appearance of the fins 310 on an ultrasound imaging device 100 may take various forms. However, in the example embodiment illustrated in the various drawings herein (e.g., as most prominently shown in FIG. 1A), the fins may, alone or in combination with other visual elements, primarily provide a distinctive visual and decorative appearance for the ultrasound imaging device 100. For example, the layout, arrangement, and positioning of the fins 310 may provide visual distinctiveness for the illustrated example embodiment of the ultrasound imaging device 100.

Additionally, configuring the exterior surface 204 to have a number of fins 310 may increase the surface area of the exterior surface 204 of the front shell 202 and the housing 102 overall, so as to further improve heat dissipation. For example, the fins 310 added to the exterior surface 204 of the front shell 202 may increase the surface area of the exterior surface of the entire housing 102 by at least 30%. In one example embodiment, the fins 310 added to the front shell 204 increases the surface area of the housing 102 by 33%. As noted above, for example, in some embodiments, the total exterior surface of the housing 102 may have surface area of at least 31,525 mm$^2$ (inclusive of the grip portion 170 shown in FIG. 1A that may be covered with rubber in some embodiments).

Further, the presence of the fins 310 may provide texture on the exterior surface of the housing 102 where there may otherwise be a smooth surface. As compared to traditional wired ultrasound imaging systems where the ultrasound probe may be grasped at via an attached cable, this texture may allow a wireless ultrasound imaging device 100 to be better gripped or picked up by ultrasound operators.

Referring still to FIG. 3B, shown there are the positions of certain regions of the exterior surface 204 of the front shell 202 relative to the post 230a, 230b on the interior surface 206 of the front shell 202. For example, as shown, the smooth region 315 of the exterior surface 204 may be provided opposite the post 230b. Additionally, it may be possible to position the fins 310 on a region of the exterior surface 204 opposite a location on the interior surface 206 that is directly coupled to the post 230a. Configuring the fins 310 to be directly opposite a post 230a may allow heat to be transferred more easily from the post 230a towards a region of the exterior surface 204 having increased surface area, so that the heat can be more easily dissipated therefrom. At the same time, the increased surfaced area created by the fins 310 may spread the heat channeled by the post 230a over a larger surface area and reduce the likelihood of significant hot spots being created on the exterior surface 204 at regions directly opposite the area where the post 230a is coupled. This effect of spreading the heat over a larger area may be further enhanced by having the finned region of the exterior surface 204 be larger in size than the area on the interior surface 206 that is directly coupled to the post 230a. Additionally, the finned region may increase the distance (e.g., create a small gap) between the surface immediately opposite where a post 230a is coupled and the surface that comes into contact with the ultrasound operator. This small air gap may reduce the heat sensation felt by the ultrasound operator.

Figure 4A:
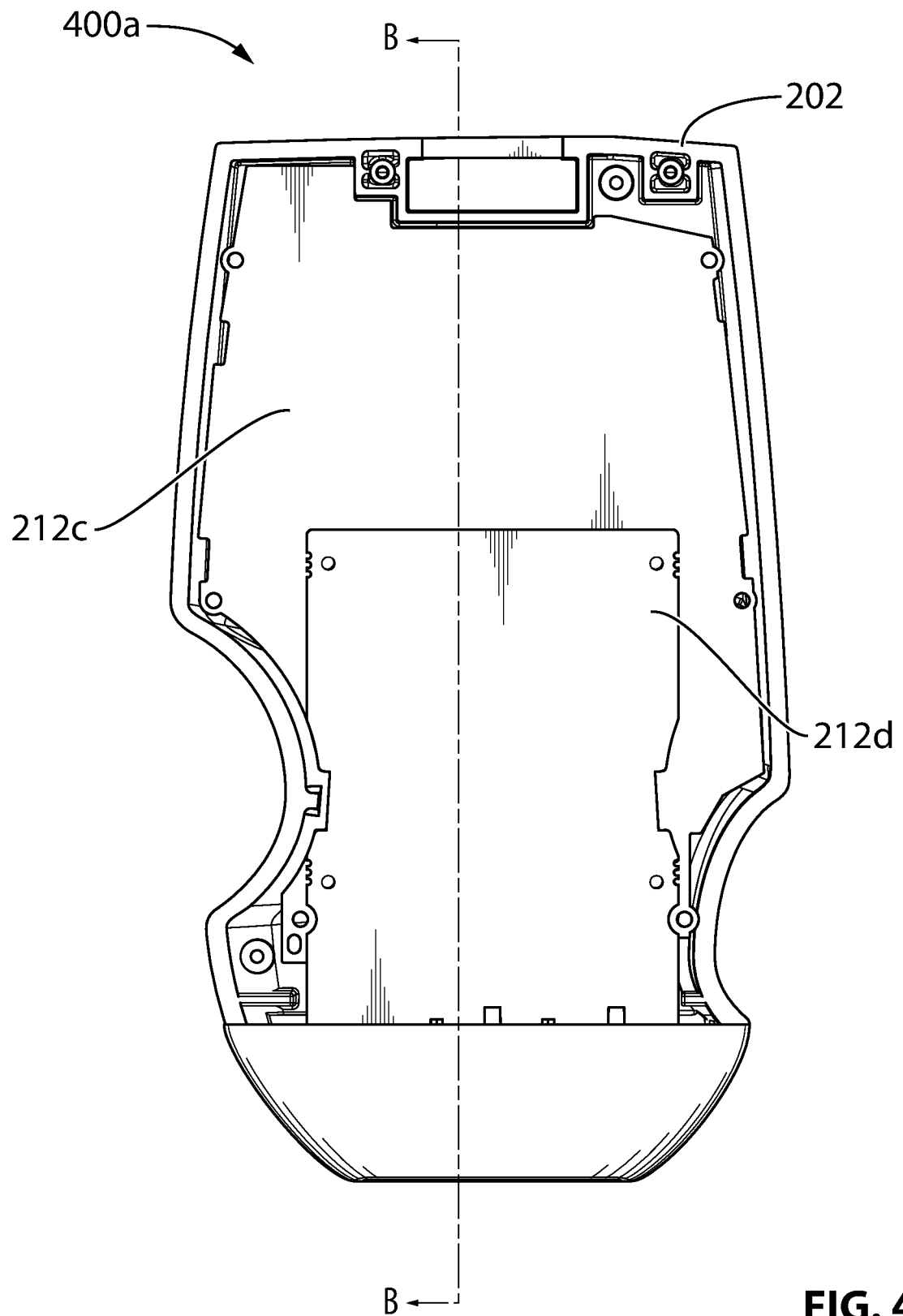
FIG. 4A shows a rear view of a partially-assembled ultrasound imaging device of FIGS. 1A-1D, in accordance with at least one embodiment of the present invention.

Referring to FIG. 4A, shown there generally as 400a is a rear view of a partially-assembled ultrasound imaging device of FIGS. 1A-1D, in accordance with at least one embodiment of the present invention. FIG. 4A generally shows an interior view of when the components of FIGS. 2A-2C are assembled. From the illustrated rear view, the front shell 202, transducer cap 210, and circuit boards 212c, 212d can be seen.

Figure 4B:
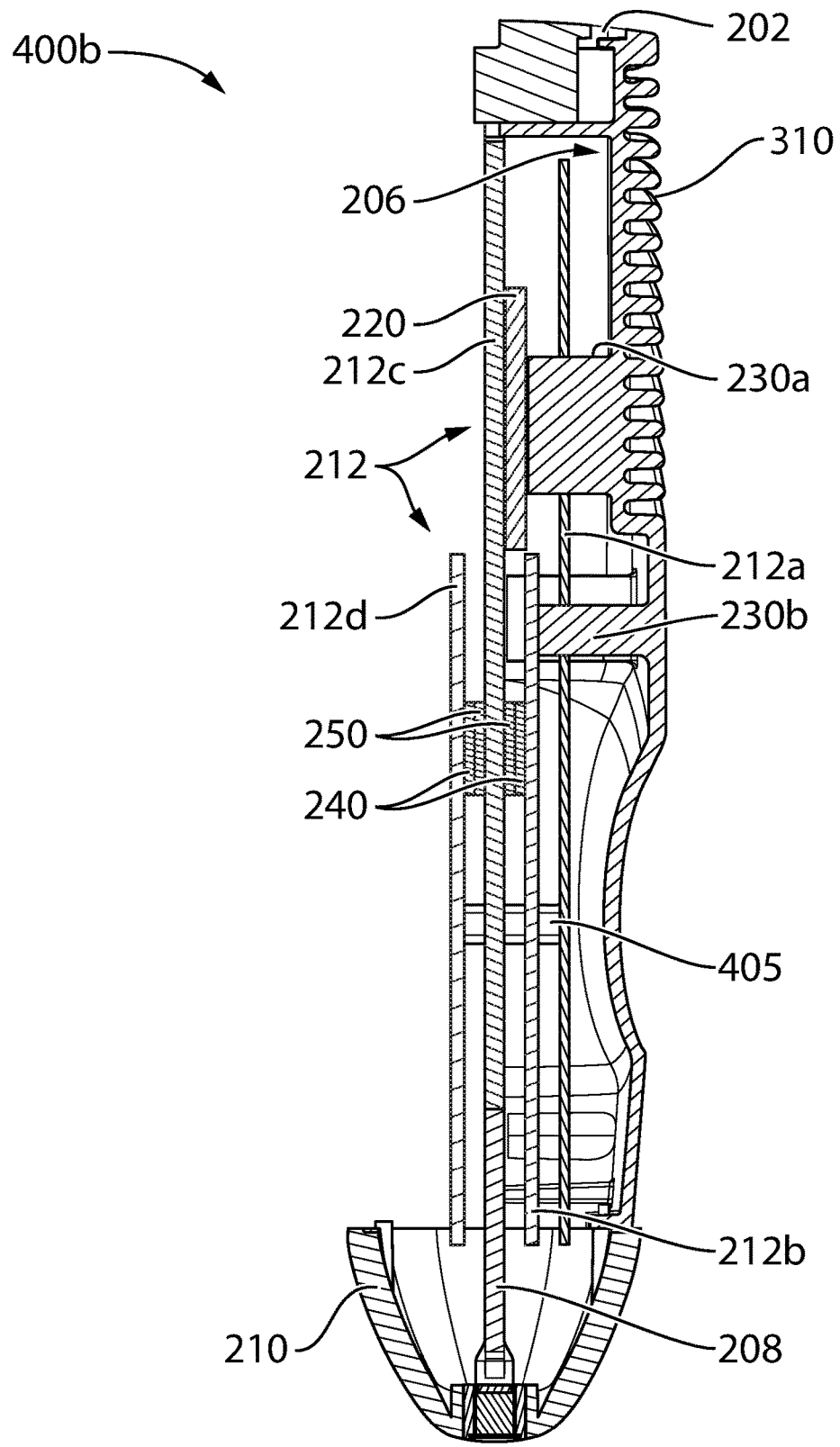
FIG. 4B shows a cross-sectional view of the partially-assembled ultrasound imaging device shown in FIG. 4A along the line B-B, in accordance with at least one embodiment of the present invention.

Referring to FIG. 4B, shown there generally as 400b is a cross-sectional view of the partially-assembled ultrasound imaging device shown in FIG. 4A along the line B-B, in accordance with at least one embodiment of the present invention. Referring briefly also to FIG. 3A, it can be seen that the section line B-B may generally cut through portions of posts 230a and 230b. FIG. 4B provides a view similar to that shown in FIG. 3B, except a number of additional components shown in FIGS. 2A-2C are also shown.

In FIG. 4B, it can be seen that posts 230a, 230b are directly coupled to the interior surface 206 of the front shell 202. Circuit board 212a can be seen to be fitting around the posts 230a, 230b, and processor 220 provided on circuit board 212c is mated directly to the post 230a. Post 230b is mated to an upper region of the surface of circuit board 212b that faces the front of the ultrasound imaging device 100. Also, the ADCs 240 provided on boards 212b, 212d are mated to circuit board 212c via thermal pads 250. As discussed above, the thermal pads 250 may be mated to the ground plane of the circuit board 212c, which is then indirectly mated to additional posts 230c, 230c' (not shown in FIG. 4B) through the ground plane of the circuit board 212c for heat transfer. FIG. 4B also shows the coupling of the transducer array 208 to circuit board 212c, and the transducer cap 210.

Also viewable in FIG. 4B are a number of metallic spacers 405 (not shown in earlier figures) which may allow the circuit boards 212d, 212c, 212b, 212a to be held together. In such embodiments, the circuit boards 212 may be provided with mounting holes (not shown) which are connected to the ground planes of the various circuit boards (including circuit board 212c). Metallic screws (not shown in FIG. 4B) may then be used to thread through the metallic spacers 405 and secure the circuit boards 212d, 212c, 212b, 212a together. One or more of the circuit boards 212d, 212c, 212b, 212a may then be secured to the housing 102 (e.g., to the front shell 202 and/or the rear shell 502) through the same or additional mounting holes provided on the circuit boards 212d, 212c, 212b, 212a, also using metallic screws. The metallic screws travelling through multiple circuit boards 212 and metallic spacers 405 and eventually having indirect contact with the housing 102 may provide an additional heat transfer path from various ICs provided on the circuit boards 212d, 212c, 212b, 212a to the housing 102, and thereby further improve heat dissipation. In various embodiments, the metallic spacers 405 may be any form of suitable metallic component that allows for heat transfer. For example, the metallic spacer 405 may be an bushing or a bolt, and either threaded or unthreaded.

In some embodiments, the circuit boards 212d, 212c, 212b, 212a may be configured to have exposed ground planes in areas where the circuit boards come into contact with the metallic spacers 405. Such a configuration may enhance heat transfer amongst the multiple circuit boards 212d, 212c, 212b, 212a through the metallic spacers 405, and specifically, enhance heat transfer towards the ground plane of circuit board 212c. As discussed above in relation to FIG. 2C, the ground plane of 212c is coupled to posts 230c, 230c' provided on the front shell 202 of the housing 102, so that heat can be dissipated therefrom. As illustrated in FIG. 4B, the metal spacers 405 are shown in the cross-sectional view along line B-B of FIG. 4A. However, the metal spacers 405 and corresponding mounting holes may be provided at any area of one or more of the circuit boards 212d, 212c, 212b, 212a that allows a common screw or other mechanism to bind the one or more of the circuit boards 212d, 212c, 212b, 212a together and/or to the housing 102.

Additionally, there may be a number of connectors (not shown) that allow one or more of the various circuit boards 212d, 212c, 212b, 212a to be coupled together for electrical communication. These various connectors may have metallic ground pins that may provide a further heat transfer mechanism amongst the ground planes of the circuit boards 212d, 212c, 212b, 212a, and allow heat to be channeled towards the ground plane of circuit board 212c which is physically coupled to posts 230c, 230c'.

As mentioned above, to provide ultrasound images with high quality and desired tissue penetration, the ultrasound image device 100 may be provided with a number of ADCs 240b, 240d, and a processor 220 that is capable of carrying heavy loads when performing image processing. For example, in some embodiments, the ADCs 240b, 240d, processor 220, and/or other ICs may collectively or individually consume at least 3 watts of power (e.g., while imaging or in any other active mode). In one example embodiment, a programmable System on a Chip (SoC) may be used and such IC may consume 3.5-4.5 watts of power while imaging. This level of power consumption may be considered to be relatively high for portable wireless devices; and the present embodiments may be particularly applicable in such situations to dissipate the higher levels of heat generated by the increased power consumption.

While the embodiments described herein may be employed in any context where heat is generated from ICs within the housing 102, the techniques discussed may be particularly applicable in embodiments where it is desired to dissipate heat generated from general purpose ICs. Unlike application-specific integrated circuits (ASICs) which can be designed to perform within particular heat parameters while still carrying heavy loads, general purpose ICs may not be designed in such a manner and, as a result, may generate more heat. However, use of general-purpose ICs allows ultrasound imaging devices 100 to be designed and constructed in a more straightforward and cost-effective manner. As such, the techniques described herein may facilitate heat dissipation using general-purpose ICs without resorting to the expense and effort of designing a dedicated ASIC that outputs lower heat. Indeed, the improved heat dissipation mechanisms discussed herein may reduce the possibility of IC failures and/or the surface temperature of the housing 102 being non-compliant with applicable safety regulations (for ultrasound imaging devices 100 generally, and in particular embodiments where general-purpose ICs are used).

Figure 5A:
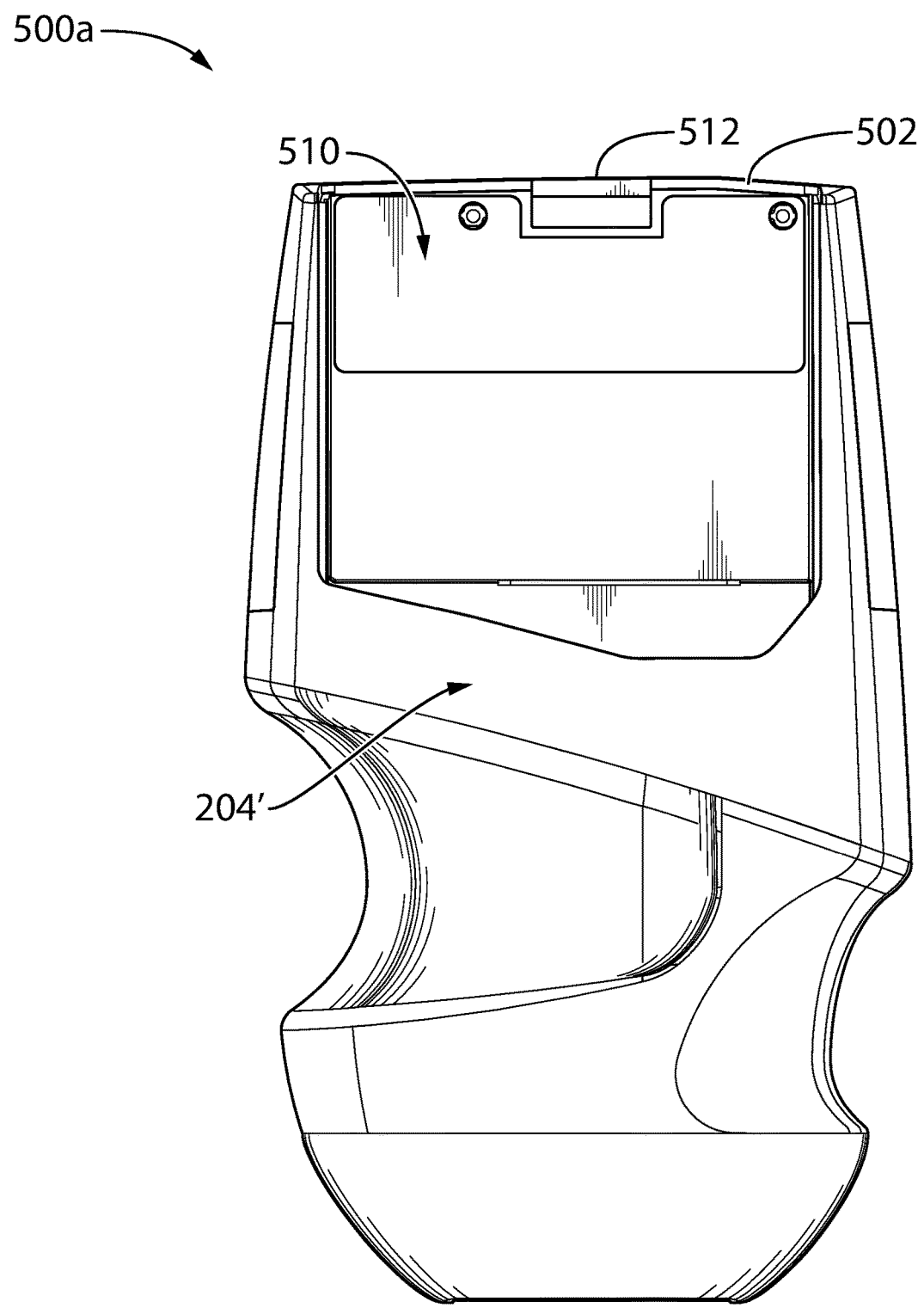
FIGS. 5A-5B show exterior and interior views of the rear shell that forms part of the housing of the ultrasound imaging device of FIGS. 1A-1D, in accordance with at least one embodiment of the present invention.

Referring to FIG. 5A, shown there generally as 500a is an exterior view of the rear shell 502 that forms part of the housing 102 of the ultrasound imaging device of FIGS. 1A-1D, in accordance with at least one embodiment of the present invention. To provide substantially uniform thermal conductive properties across the entire housing 102, in some embodiments, the rear shell 502 may also be made of the same metal as the front shell 202. As shown, the rear shell 502 may have an exterior surface 204' that includes a slot 510 for receiving the removable battery 106 (not shown in FIG. 5B, but shown included in the view of FIG. 1B). The rear shell 502 may provide a latch 512 for securing the battery 106 in place when it is placed within the slot 510. It will be understood by persons skilled in the art that a latch 512 is simply one way of securing the battery 106 in place when it is in the slot 510, and that other mechanisms may be possible. Moreover, in some embodiments, the ultrasound imaging device 100 may not have a removable battery, and instead, an internal battery may be provided.

Figure 5B:
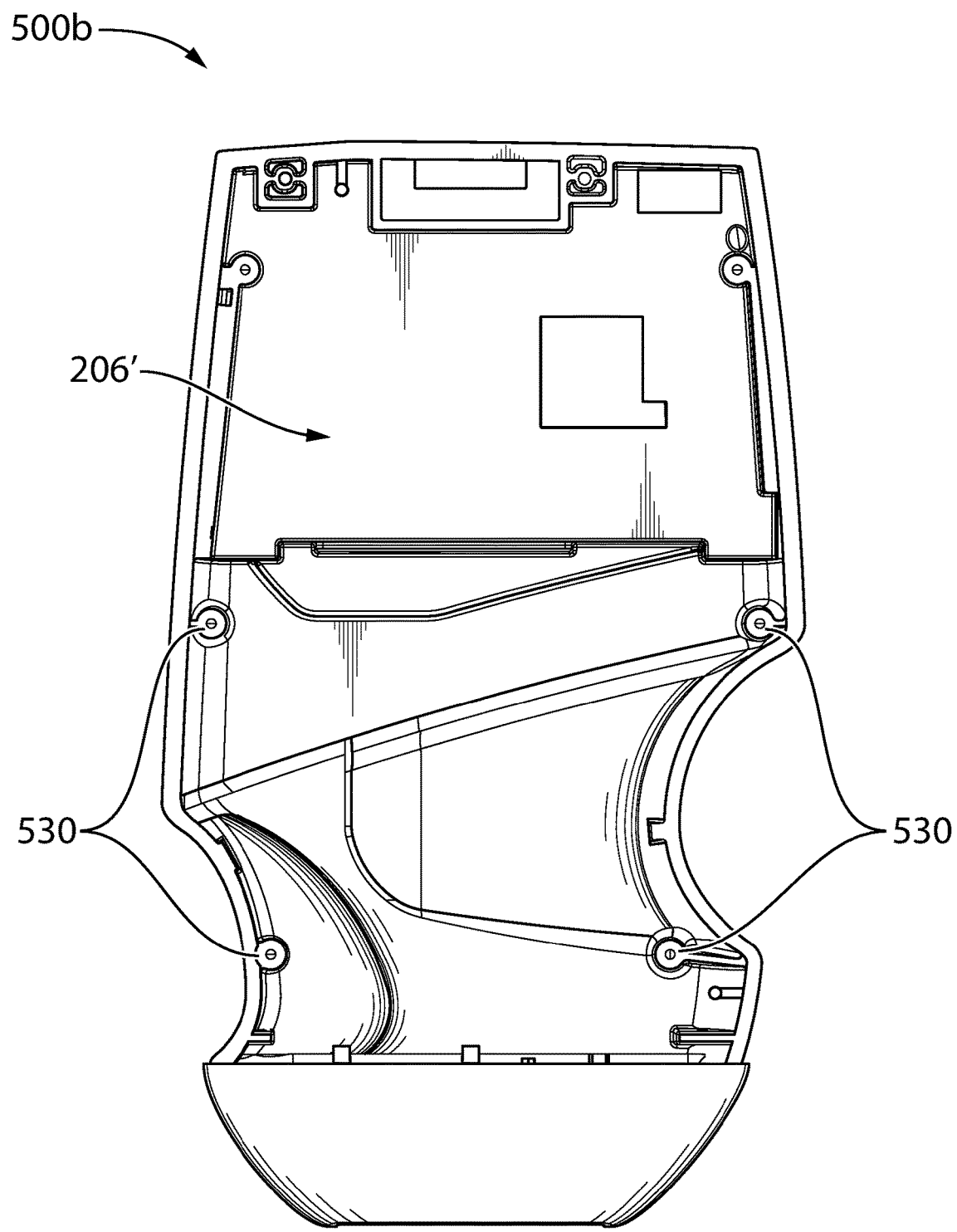

Referring to FIG. 5B, shown there generally as 500b is an interior view of the rear shell 502 that forms part of the housing 102 of the ultrasound imaging device of FIGS. 1A-1D, in accordance with at least one embodiment of the present invention. The rear shell 502 may have an interior surface 206' which is placed adjacent the circuit boards 212d, 212c shown in FIG. 4A when the rear shell 502 mates with the front shell 202 and the ultrasound imaging device 100 is in assembled form. Referring briefly also to FIG. 4B, the circuit boards 212a, 212b, 212c, 212d may be secured together (e.g., via, or as separated by, metallic spacers 405) to form a circuit board assembly. The circuit board assembly may then be secured to the rear shell 502 (and housing 102) to allow for an additional heat transfer path from the ICs to the housing 102. In some embodiments, the metallic screws that secure the circuit board assembly together may also be used to secure the circuit boards to the housing 102. In some embodiments, there may be one set of screws that binds the circuit boards 212d, 212c, 212b, 212a together, and another set of screws that bind the bounded circuit board assembly to the housing 102. As shown in FIG. 5B, there are a number of mounting holes 530 that may be used to receive metallic screws so as to allow for the circuit board assembly to be secured to the rear shell 502.

Referring simultaneously to FIG. 1C, FIG. 4B, and FIG. 5A, it can be seen that when the ultrasound imaging device 100 is in assembled form, the battery 106 (as shown in FIG. 1C) that powers the ultrasound imaging device 100 is positioned on a side of the ultrasound imaging device 100 that is opposite the fins 310. Since the battery 106 is typically made of a material that is less thermally conductive than the metallic surface 204' (as shown in FIG. 5A) of the housing 102, it may be difficult for heat to travel through the battery 106 to dissipate from the exterior surface 204' of the rear shell 502. The heat generated by the internal components of the ultrasound imaging device 100 may thus generally be channeled to the front shell 202 (as shown in FIG. 1C) for dissipation. The positioning of the posts 230 to couple directly with the interior surface 206 of the front shell 202 (as shown in FIG. 4B) may thus assist with such channeling of heat. In addition, the placement of fins 310 on an area of the exterior surface of the housing 102 opposite the side of the ultrasound imaging device 100 where the battery 106 is positioned may provide a greater surface area for dissipating the additional heat that would not be able to be channeled towards the rear shell 502 due to the battery 106.

Figure 6A:
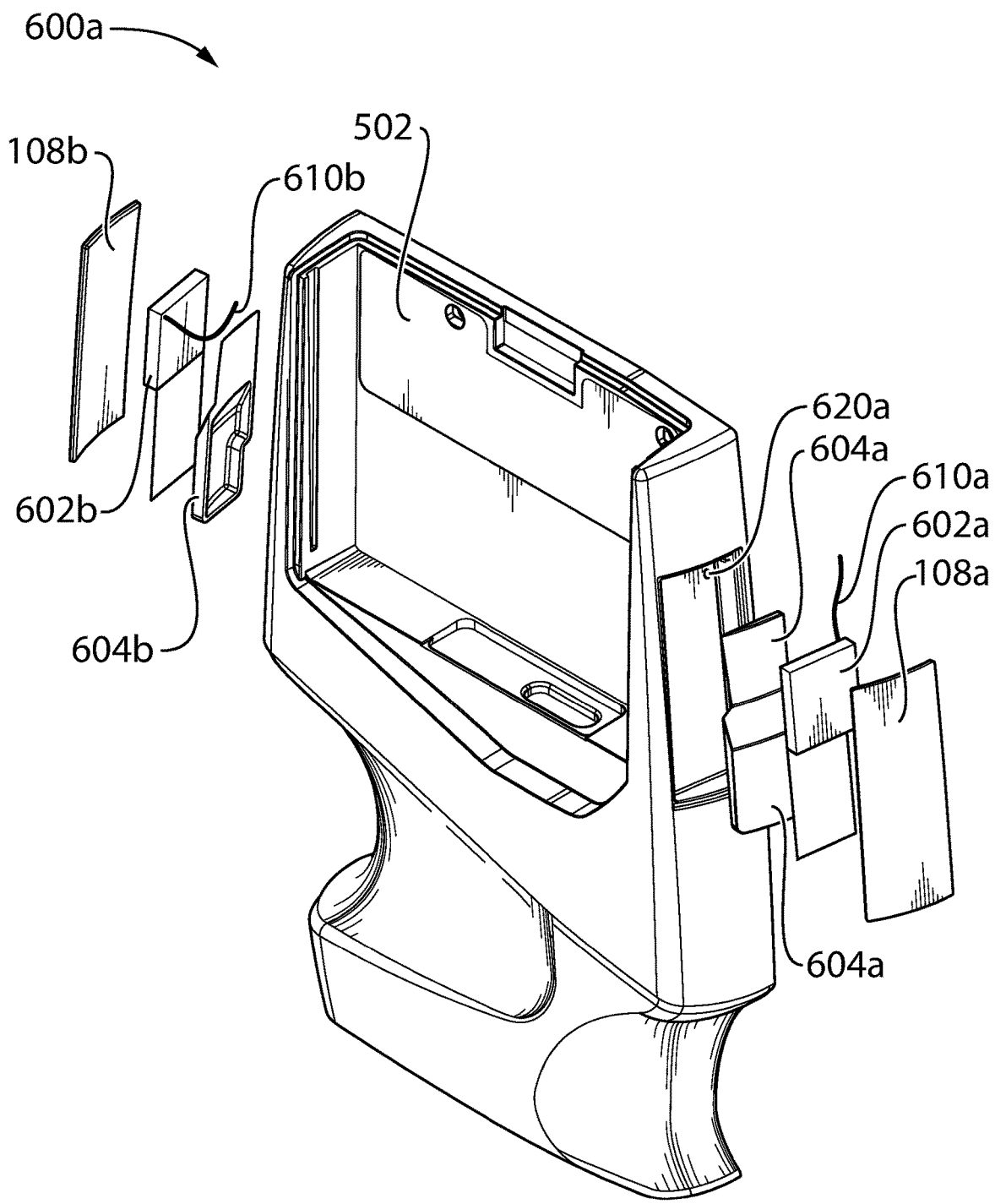
FIG. 6A shows an exterior perspective exploded view of the rear shell shown in FIGS. 5A-5B, in accordance with at least one embodiment of the present invention.

Referring to FIG. 6A, shown there generally as 600a is an exterior perspective exploded view of the rear shell 502 shown in FIGS. 5A-5B, in accordance with at least one embodiment of the present invention. As discussed above in relation to FIG. 1C, the rear shell may have recesses on its sides to allow for placement of antennas for wireless communications. While a housing 102 that is made substantially of metal may improve heat dissipation, metal is generally a ferromagnetic material that may interfere with proper operation of antennas if the antennas are placed within the metal housing 102. The recesses may thus allow the housing 102 to be made substantially of metal (and achieve as much heat dissipation as possible), but also provide a mechanism for placement of the antennas on the exterior of the housing 102 so that wireless communications may not be unduly impeded.

As compared to some mobile communication devices (e.g., mobile phones) that have metallic backings, a larger portion of the housing 102 of the ultrasound imaging device 100 may be made of metal. For example, in the illustrated embodiments, the entire housing 102 (except for the transducer cap 210) may be made of metal. Whereas a traditional mobile communications device may typically have a screen or other gaps in their housing that would allow wireless signals to be effectively transmitted from an antenna positioned within a metal housing, the mobile wireless ultrasound device 100 of the present embodiments does not have a screen or such gaps. Instead, a larger portion of the housing 102 may be constructed of metal to better facilitate dissipation of the higher level of heat generated by the higher wattage processing components (e.g., ADCs 240b, 240d) in an ultrasound imaging device 100.

In the illustrated embodiment of FIG. 6A, there may be antennas 602a, 602b, which are to be placed within recesses on the two sides of rear shell 502. To provide improved operation of the antennas 602a, 602b, there may also be provided shims 604a, 604b to space the respective antenna 602a, 602b away from the metallic rear shell 502. In various embodiments, the antennas 602a, 602b may provide wireless communications on various frequencies (e.g., 2.4 Ghz or 5 Ghz) that are suitable to enable communications using any wireless communication protocols (including Wi-Fi™ or Bluetooth™). In various embodiments, a single antenna 602a may be a wireless antenna module that includes multiple types of antennas that communicate on multiple frequencies and/or protocols (e.g., the module may include both Wi-Fi™ and Bluetooth™ antennas). In such embodiments, the same antenna module may be added in both the left and right recesses of the rear shell 502 to allow for improved radio link performance using multiple-in and multiple-output (MIMO) methods. The shape of the recess may be configured to fit any type of suitable antenna module that allows for desired wireless communications. For example, in one example embodiment, the antenna module 001-0021, manufactured by LSR™ may be used.

Referring still to FIG. 6A, covers 108a, 108b may be placed over the antennas 602a, 602b so as to form substantially flat side surfaces of the ultrasound imaging device 100. The covers 108a, 108b may generally be made of non-ferromagnetic material so as to not interfere with the operation of the antennas 602a, 602b. In some embodiments, the covers 108a, 108b may form a seal with the adjacent exterior surfaces of the housing 102 so as to prevent ingress (e.g., from liquid or dust). In embodiments where the slot 510 for the battery 106 is constructed to also be sealed when the battery 106 is in place, the entire ultrasound imaging device 100 may be considered to be protected from ingress into the interior of the device 100. In some embodiments, the housing may have an International Protection Marking (IP Code) ingress rating of at least IPX7.

As shown in FIG. 6A, each of the antennas 602a, 602b may have corresponding connector wires 610a, 610b for connecting to and communicating with the electronic components inside the housing 102. To allow for the connector wires 610a, 610b to electronically couple with internal electronic components, the rear shell 502 may provide small openings in the recesses where the antennas 602a, 602b are to be placed. The connector wires 610a, 610b may then be threaded through these openings to the interior of the housing 102 so that they may, for example, connect with circuit boards 212a, 212b, 212c, 212d (as shown in earlier figures) and other ICs provided thereon.

As discussed above, it may be possible to use the same antenna modules (having both Wi-Fi™ and Bluetooth™ antennas) in each of the left and right recesses provided on the rear shell 502. However, if the same antenna module is used, the connector wires 610a, 610b may not always be positioned towards the same surface of the rear shell 502 when placed within the recesses. For example, in the view and orientation shown in FIG. 6A, the connector wire 610a is shown as being provided on the top right corner of the antenna module 602a. To allow for this connector wire 610a to thread into the interior of the housing 102, an opening 620a may be provided in the corresponding corner of the recess. As shown in FIG. 6A, the opening may be provided on a corner of the recess that is proximate the interior surface of the rear shell 502. In contrast, if the same antenna module is placed in the opposite recess provided on the rear shell 502, the connector wire 610b provided with the antenna module 602b may be flipped along its lengthwise axis, so that connector wire 610b extends from the upper left hand corner of the antenna module 602b. The connector wire 610b may then be oriented towards the exterior surface of the rear shell 502 instead of the interior surface of the rear shell 502. In some embodiments, an opening 620b may be provided in the corresponding corner of that recess, which is proximate the exterior surface of the housing 102. This opening 620b may be more clearly viewable in FIG. 6B.

Figure 6B:
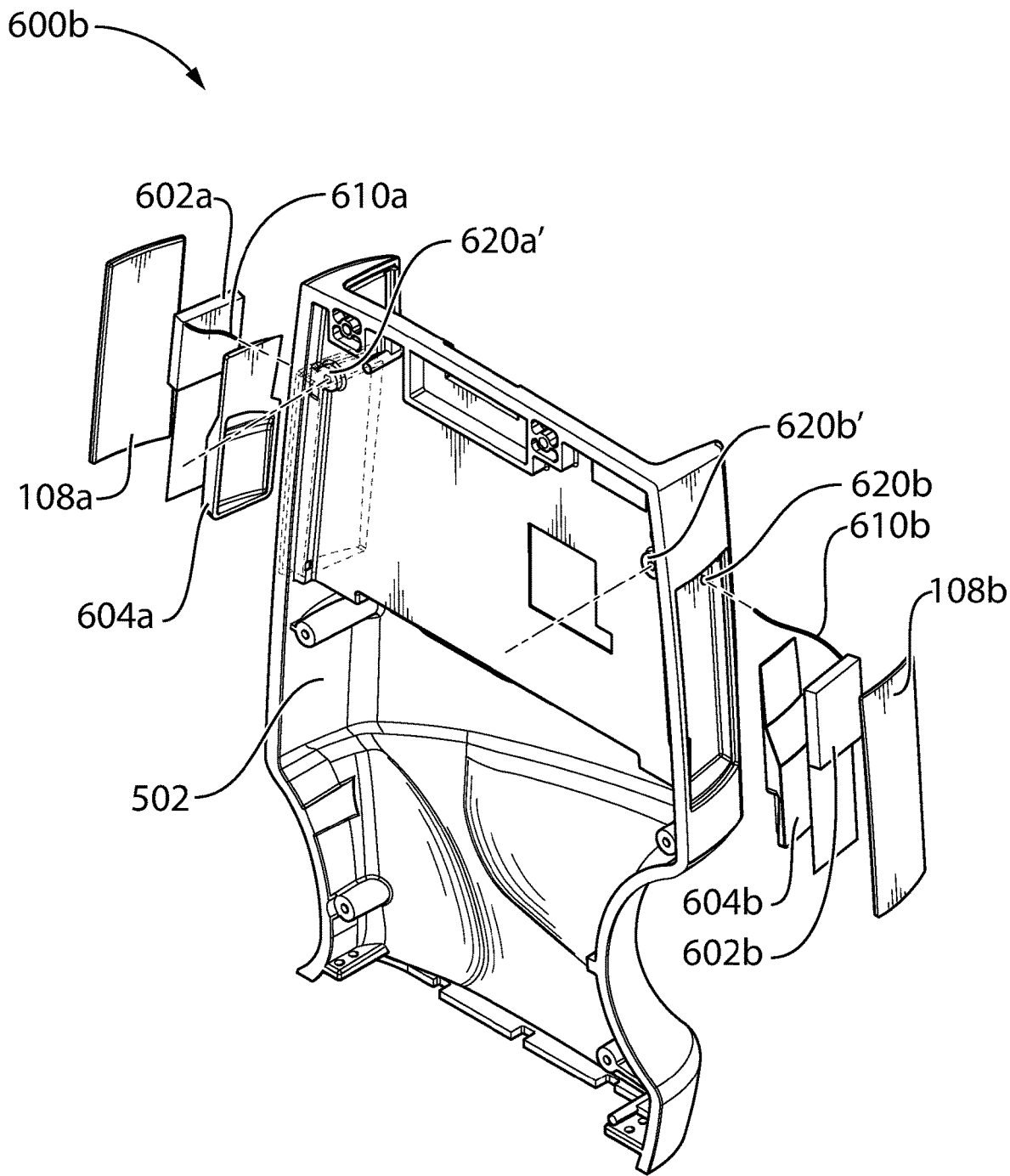
FIG. 6B shows an interior perspective exploded view of the rear shell shown in FIGS. 5A-5B, in accordance with at least one embodiment of the present invention.

Referring simultaneously to FIG. 6B, shown there generally as 600b is an interior perspective exploded view of the rear shell shown in FIGS. 5A-5B, in accordance with at least one embodiment of the present invention. The view 600b shows the same components of FIG. 6A, but flipped along the longest axis of the rear shell 502. The antenna 602a, shim 604a, and cover 108a are illustrated. As shown, a corresponding end 620a' of the opening 620a (as shown in FIG. 6A) may be provided on the interior surface of the rear shell 502, so as to allow the connector wire 610a to protrude into the interior surface of the housing 102.

FIG. 6B also shows the antenna 602b, shim 604b, and cover 108b that may be placed in the opposite recess of the rear shell 502. As shown, the opening 620b may be provided near a corner of the recess that is proximate the exterior surface of the rear shell 502, so as to align with the positioning of the connector wire 610b on the antenna 602b. The opening 620b may tunnel through the body of the rear shell 502 to its corresponding end 620b' (e.g., through the depth of the shortest axis of the rear shell 502) so as to allow the connector wire 610b to be presented to the interior surface of the housing 102. This tunneling may not be required for the opening 620a because the opening 620a is provided on a corner of the recess that is already adjacent the interior surface of the rear shell 502.

Figure 7:
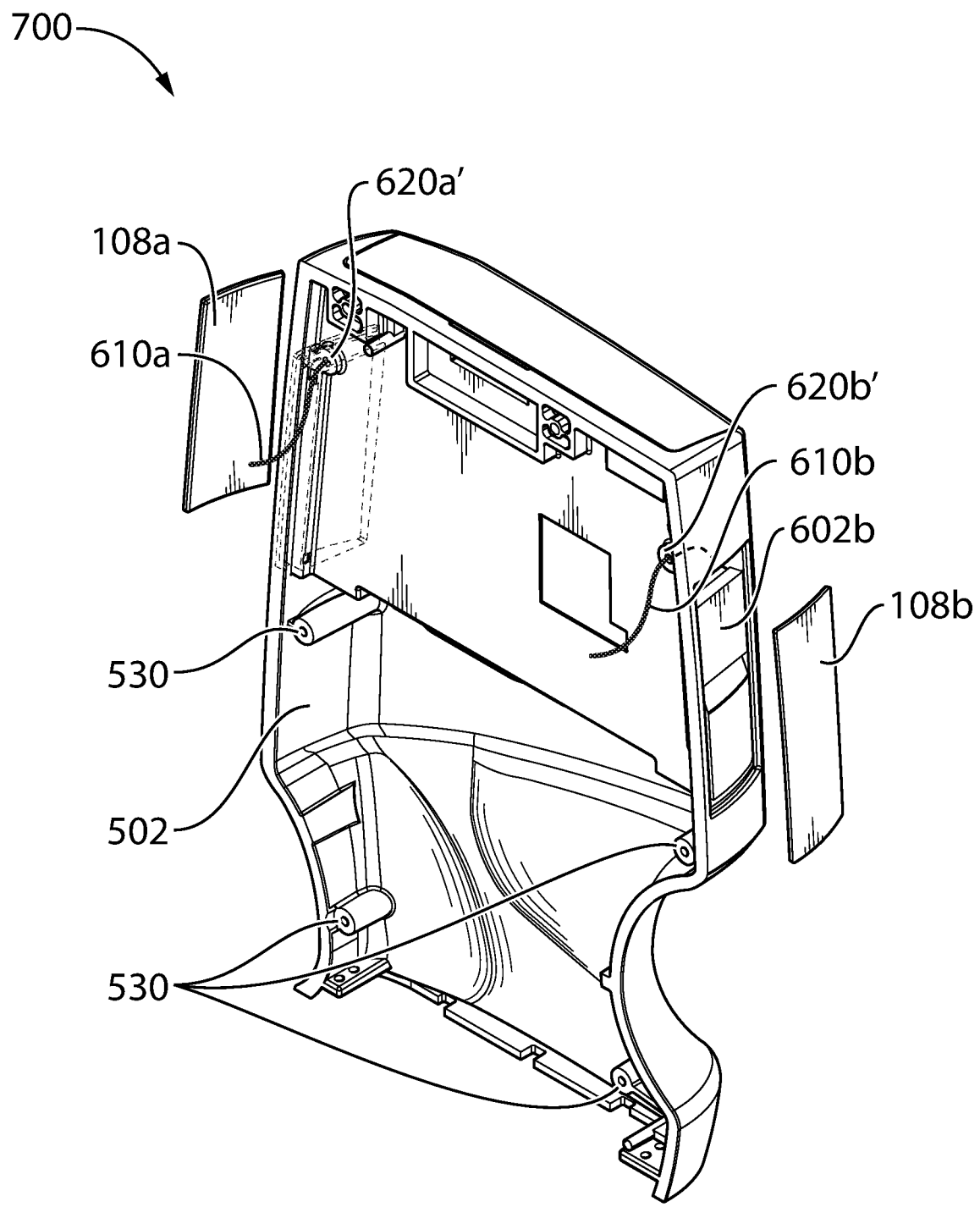
FIG. 7 shows an interior perspective view of a partially-assembled configuration of the components shown in FIGS. 6A-6B, in accordance with at least one embodiment of the present invention.

Referring to FIG. 7, shown there generally as 700 is an interior perspective view of a partially-assembled configuration of the components shown in FIGS. 6A-6B, in accordance with at least one embodiment of the present invention. FIG. 7 shows the antenna 602b being provided within in the right-hand recess of the rear shell 502. In assembled form, the connector wire 610b of the antenna 602b may be inserted in opening 620b (not shown in FIG. 7) provided near the exterior surface of the rear shell 502, so as to tunnel through the body of the rear shell 502 and protrude through the opposite end 620b' of the opening 620b. Also viewable in FIG. 7 is the connector wire 610a of antenna 602a (shown in FIGS. 6A and 6B) that protrudes through opening 620a (as shown in FIG. 6A) and exits at the opposite end 620a' on the interior surface of the rear shell 502. Also viewable in FIG. 7 are the covers 108a, 108b which may be placed over the recesses, and mounting holes 530 to which circuit boards 212 may be mounted, as discussed above.

Interpretation of Terms

Unless the context clearly requires otherwise, throughout the description and the claims:
"comprise", "comprising", and the like are to be construed in an inclusive sense, as opposed to an exclusive or exhaustive sense; that is to say, in the sense of "including, but not limited to";
"connected", "coupled", or any variant thereof, means any connection or coupling, either direct or indirect, between two or more elements; the coupling or connection between the elements can be physical, logical, or a combination thereof;
"herein", "above", "below", and words of similar import, when used to describe this specification, shall refer to this specification as a whole, and not to any particular portions of this specification;
"or", in reference to a list of two or more items, covers all of the following interpretations of the word: any of the items in the list, all of the items in the list, and any combination of the items in the list;
the singular forms "a", "an", and "the" also include the meaning of any appropriate plural forms.

Unless the context clearly requires otherwise, throughout the description and the claims:
Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such alterations, modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. A wireless ultrasound imaging apparatus, comprising:
    a body with an imaging end, a non-imaging end, and a side surface between the imaging end and the non-imaging end, the side surface being holdable during operation of the ultrasound imaging apparatus;
    a transducer array positioned at the imaging end of the body;
    at least one integrated circuit (IC) operatively connected to the transducer array; and
    an antenna operatively connected to the at least one IC, the antenna for providing wireless communication of ultrasound image data;
    wherein the body comprises a metallic housing, the metallic housing enclosing the transducer array and the at least one IC, and wherein the metallic housing comprises an interior surface opposite the holdable side surface of the body;
    wherein during imaging, power is consumed by the at least one IC, to generate ultrasound image data for wireless transmission via the antenna; and
    wherein a post is disposed between the at least one IC and the interior surface that is opposite the holdable side surface of the body, the post being coupled directly to the interior surface of the metallic housing so that heat, generated as a result of the consumption of power by the at least one IC during imaging, is transferred via the post to the metallic housing and dissipated.

2. The wireless ultrasound imaging apparatus of claim 1, wherein the metallic housing comprises a material having a thermal conductivity of between 55 to 167 watts per meter kelvin (W/(m·K)) and a density of between 1.77 to 5 grams per cubic centimeter (g/cm$^3$).

3. The wireless ultrasound imaging apparatus of claim 2, wherein the material comprises an aluminum alloy.

4. The wireless ultrasound imaging apparatus of claim 2, wherein the material comprises a magnesium alloy.

5. The wireless ultrasound imaging apparatus of claim 1, wherein the power consumed by the at least one IC is between 3 to 4.5 watts of power.

6. The wireless ultrasound imaging apparatus of claim 1, wherein the metallic housing comprises a grip portion and a non-grip portion, and the grip portion is covered with an insulating polymer-based material, and the non-grip portion is uncovered such that the holdable side surface of the metallic housing is exposed at the non-grip portion.

7. The wireless ultrasound imaging apparatus of claim 1, wherein the holdable side surface of the metallic housing forms the outermost surface of the wireless ultrasound imaging apparatus, and the holdable side surface comprises a recess for placement of the antenna.

8. The wireless ultrasound imaging apparatus of claim 7, wherein a shim is positioned in the recess between the metallic housing and the antenna to space the antenna away from the metallic housing.

9. The wireless ultrasound imaging apparatus of claim 7, wherein a non-ferromagnetic cover is placed over the antenna, and wherein the non-ferromagnetic cover forms a seal with an adjacent exterior surface of the metallic housing to prevent ingress into the interior of the wireless ultrasound imaging apparatus.

10. The wireless ultrasound imaging apparatus of claim 1, wherein the at least one IC comprises an Analog to Digital Converter (ADC) and a graphic processor.

11. The wireless ultrasound imaging apparatus of claim 1, wherein the at least one IC comprises a programmable System on a Chip (SoC).

12. The wireless ultrasound imaging apparatus of claim 1, wherein the metallic housing comprises a front shell and a rear shell, and at least one of the front shell or the rear shell is formed to receive a removable battery.

13. The wireless ultrasound imaging apparatus of claim 1, wherein the metallic housing comprises a slot for receiving a removable battery.

14. The wireless ultrasound imaging apparatus of claim 13, wherein the wireless ultrasound imaging apparatus is sealed when the removable battery is positioned in the slot, and the wireless ultrasound imaging apparatus with the removable battery in place is protected from ingress into the interior of the wireless ultrasound imaging apparatus.

15. A method of facilitating dissipation of heat in a wireless ultrasound imaging apparatus, the method comprising:
    providing a body for the wireless ultrasound imaging apparatus, the body comprising an imaging end, a non-imaging end, and a side surface between the imaging end and the non-imaging end, with the side surface being holdable during operation of the ultrasound imaging apparatus, the body comprising a metallic housing enclosing a transducer array positioned at the imaging end of the body and at least one integrated circuit (IC) operatively connected to: the transducer array and an antenna, the antenna for providing wireless communication of ultrasound image data, wherein the metallic housing comprises an interior surface opposite the holdable side surface of the body; and
    activating the at least one IC during operation of the wireless ultrasound imaging apparatus, wherein power is consumed by the activated at least one IC to generate ultrasound image data for wireless transmission via the antenna, and wherein heat generated as a result of the consumption of power by the at least one IC during imaging is transferred to the metallic housing and dissipated therefrom via at least one post that is disposed between the at least one IC and the interior surface of the metallic housing that is opposite the holdable side surface of the body, the post being coupled directly to the interior surface of the metallic housing.

16. The method of claim 15, wherein the metallic housing comprises a material having a thermal conductivity of between 55 to 167 watts per meter kelvin (W/(m·K)) and a density of between 1.77 to 5 grams per cubic centimeter (g/cm$^3$).

17. The method of claim 15, wherein the power consumed by the at least one IC is between 3 to 4.5 watts of power.

18. The method of claim 15, wherein the metallic housing comprises a front shell and a rear shell, and at least one of the front shell or the rear shell is formed to receive a removable battery.

19. The method of claim 15, wherein the metallic housing comprises a slot for receiving a removable battery.

20. The method of claim 19, wherein the wireless ultrasound imaging apparatus is sealed when the removable battery is positioned in the slot, and the wireless ultrasound imaging apparatus, with the battery in place, is protected from ingress into the interior of the wireless ultrasound imaging apparatus.

21. The method of claim 15, wherein the holdable side surface of the metallic housing that forms the outermost surface of the wireless ultrasound imaging apparatus, and the holdable side surface comprises a recess for placement of the antenna.

22. The method of claim 21, wherein a non-ferromagnetic cover is placed over the antenna, and wherein the non-ferromagnetic cover forms a seal with an adjacent exterior surface of the metallic housing to prevent ingress into the interior of the wireless ultrasound imaging apparatus.

\* \* \* \* \*